United States Patent
Honjo et al.

(10) Patent No.: US 12,090,233 B2
(45) Date of Patent: Sep. 17, 2024

(54) TIMED-ELUTION MASKING PARTICLES AND ORAL PHARMACEUTICAL COMPOSITION CONTAINING THE SAME

(71) Applicant: TOWA PHARMACEUTICAL CO., LTD., Osaka (JP)

(72) Inventors: Tatsuya Honjo, Osaka (JP); Megumi Murahashi, Osaka (JP); Masaki Sato, Osaka (JP); Kayo Yuminoki, Osaka (JP); Isamu Saeki, Osaka (JP); Yutaka Okuda, Osaka (JP)

(73) Assignee: TOWA PHARMACEUTICAL CO., LTD., Osaka (JP)

( * ) Notice: Subject to any disclaimer, the term of this patent is extended or adjusted under 35 U.S.C. 154(b) by 114 days.

(21) Appl. No.: 17/619,484

(22) PCT Filed: Jun. 10, 2020

(86) PCT No.: PCT/JP2020/022921
§ 371 (c)(1),
(2) Date: Dec. 15, 2021

(87) PCT Pub. No.: WO2020/255837
PCT Pub. Date: Dec. 24, 2020

(65) Prior Publication Data
US 2022/0401373 A1 Dec. 22, 2022

(30) Foreign Application Priority Data
Jun. 17, 2019 (JP) ................. 2019-111701

(51) Int. Cl.
*A61K 9/50* (2006.01)
*A61K 9/48* (2006.01)
(Continued)

(52) U.S. Cl.
CPC .......... *A61K 9/5042* (2013.01); *A61K 9/4858* (2013.01); *A61K 9/4866* (2013.01);
(Continued)

(58) Field of Classification Search
CPC .................................................. A61K 9/5042
See application file for complete search history.

(56) References Cited

U.S. PATENT DOCUMENTS 5,487,901 A 1/1996 Conte et al.
6,139,865 A * 10/2000 Friend ............... A61P 29/00
424/490
(Continued)

FOREIGN PATENT DOCUMENTS

JP 7-138150 5/1995
JP 4277904 6/2009
(Continued)

OTHER PUBLICATIONS

International Search Report issued Aug. 18, 2020 in International (PCT) Application No. PCT/JP2020/022921.

*Primary Examiner* — Benjamin J Packard
(74) *Attorney, Agent, or Firm* — Wenderoth, Lind & Ponack, L.L.P.

(57) ABSTRACT

Masking particles which comprise a drug-containing particle containing a drug, an acid, and a carbonate, the drug-containing particle being coated with a coating layer containing a water-insoluble polymer sufficiently suppress drug release in the oral cavity and pharynx, rapidly release a drug after swallowing, and easily control the release suppression time of a drug. The acid may be at least one organic acid. The carbonate may be at least one water-soluble carbonate. Oral pharmaceutical compositions include tablets, granules, fine granules, powders.

20 Claims, 10 Drawing Sheets

(51) Int. Cl.
    *A61K 31/437*    (2006.01)
    *A61K 31/5383*   (2006.01)
(52) U.S. Cl.
    CPC ............ *A61K 9/501* (2013.01); *A61K 9/5031* (2013.01); *A61K 31/437* (2013.01); *A61K 31/5383* (2013.01)

(56) References Cited

U.S. PATENT DOCUMENTS

| | | |
|---|---|---|
| 6,709,678 B2 | 3/2004 | Gruber |
| 9,050,249 B2 | 6/2015 | Yoshida et al. |
| 2005/0287211 A1 | 12/2005 | Yoshida et al. |

FOREIGN PATENT DOCUMENTS

| | | |
|---|---|---|
| WO | 02/069939 | 9/2002 |
| WO | 2005/105045 | 11/2005 |

* cited by examiner

TIMED-ELUTION MASKING PARTICLES AND ORAL PHARMACEUTICAL COMPOSITION CONTAINING THE SAME

TECHNICAL FIELD

The present invention relates to masking particles that suppress drug release in the oral cavity or pharynx, but do not suppress drug release in the stomach or intestines, and can control drug release and to an oral pharmaceutical composition comprising the masking particles. More specifically, the present invention relates to masking particles that reduce a drug taste, especially the taste of a drug having an unpleasant taste sensed at the time of taking, and to an oral pharmaceutical composition comprising the masking particles.

BACKGROUND ART

Tablets and capsules are generally used as oral pharmaceutical preparations but are difficult for elderly persons and children having low swallowing function to swallow. To address this disadvantage, orally disintegrating tablets that rapidly disintegrate in the oral cavity have been drawing attention because these tablets are easily swallowed and can be taken without water. However, the orally disintegrating tablets disintegrate in the oral cavity, and thus orally disintegrating tablets containing a drug having an unpleasant taste such as bitterness could strongly give the unpleasant taste, unfortunately. Granules, fine granules, powders, and similar dosage forms are smaller in size than tablets and capsules and thus are easily swallowed. However, these preparations have a large surface area per weight, and thus a preparation containing a drug having an unpleasant taste could strongly give the unpleasant taste, unfortunately.

Orally disintegrating tablets, granules, fine granules, powders, and similar dosage forms rapidly release a drug on contact with water in the oral cavity. Hence, some drugs are absorbed through the oral cavity or pharynx, and the blood concentration suddenly increases to cause unexpected side effects, or pharmaceutical effects vary, unfortunately.

To mask the unpleasant taste of a pharmaceutical ingredient sensed at the time of taking or to suppress the absorption of a pharmaceutical ingredient from the oral cavity or pharynx, granules, fine granules, powders, tablets, and similar dosage forms have been coated with a coating agent containing a water-insoluble polymer. When an oral pharmaceutical preparation is coated, any taste of the pharmaceutical ingredient is not sensed in the mouth, and any pharmaceutical ingredient is not absorbed from the oral cavity or pharynx. However, the coating delays the drug release, and accordingly, the drug may be insufficiently absorbed and may fail to achieve an intended pharmaceutical effect.

Drugs are generally absorbed from the stomach and intestines. The upper part of the small intestine has a larger surface area that contributes to absorption than the lower part of the small intestine and the large intestine, and the paracellular pathway is thought to have higher permeability in the upper part of the small intestine. Hence, a drug absorbed from the intestines is thought to be absorbed mainly from the upper part of the small intestine. The oral pharmaceutical preparation is therefore required to have the properties that drug release in the oral cavity is suppressed, but the drug is released before the preparation reaches the stomach or the upper part of the small intestine or while the preparation is retained in the stomach or the upper part of the small intestine. In particular, drugs acting on the stomach or intestines, such as a gastric mucosa protecting agent, an antacid, a digestant, a drug for controlling intestinal function, an anthelminthic, a gastrointestinal analgesic and antispasmodic, and a deforming agent, are required to be released before the preparation reaches the stomach or the upper part of the small intestine or while the preparation is retained in the stomach or the upper part of the small intestine.

The degree of unpleasant taste and the absorption pattern vary with the type of drug, and the residence time in the oral cavity varies with the dosage form of a preparation. Hence, the release suppression time is preferably controllable to an intended time.

Patent Literature 1 discloses, as an oral pharmaceutical composition that suppresses drug release in the oral cavity, a granular pharmaceutical composition comprising a core particle containing a drug having an unpleasant taste, at the center, a layer containing two types of water-soluble ingredients, an insolubilizing accelerator and a substance to be insolubilized, as an interlayer, and a water infiltration control layer as the outermost layer. The interlayer contains a salting out-type insolubilizing accelerator and a substance to be insolubilized by salting out or contains an acid-type insolubilizing accelerator and a substance to be insolubilized by the acid. According to Patent Literature 1, water does not infiltrate for a predetermined period of time into the granular composition, which is ascribable to the water infiltration control layer, and the insolubilizing accelerator helps insolubilization of the substance to be insolubilized to suppress drug dissolution, but after that, water infiltrates to release the insolubilizing accelerator, and accordingly the substance to be insolubilized recovers its intrinsic water-solubility. As a result, the drug is released.

However, the granular pharmaceutical composition taught by Patent Literature 1 is difficult to control the release suppression time of a drug to an intended time, and especially, the drug dissolution is delayed.

CITATION LIST

Patent Literature

Patent Literature 1: JP 4277904 B

SUMMARY OF INVENTION

Technical Problem

The present invention has objectives to provide masking particles that sufficiently suppress drug release in the oral cavity and pharynx, rapidly release a drug after swallowing, and easily control the release suppression time of a drug and to provide an oral pharmaceutical composition comprising the masking particles.

Solution to Problem

The inventors of the present invention have repeated intensive studies in order to solve the above problems and have found that masking particles in which particles containing a drug, an acid, and a carbonate are coated with a coating layer containing a water-insoluble polymer suppress drug dissolution in the mouth or at the pharynx ascribable to the presence of the coating layer, but subsequently, rapidly release the drug because water gradually infiltrates through the coating layer into the masking particles to cause reaction between the acid and the carbonate, and the resulting foaming destroys the masking particles.

The present invention has been completed on the basis of the above findings and provides the following [1] to [22].

[1] Masking particles comprising a drug-containing particle containing a drug, an acid, and a carbonate, the drug-containing particle being coated with a coating layer containing a water-insoluble polymer.

[2] The masking particles according to [1], wherein the acid is at least one organic acid.

[3] The masking particles according to [1] or [2], wherein the carbonate is at least one water-soluble carbonate.

[4] The masking particles according to any one of [1] to [3], wherein the acid is contained in an amount of 0.5 to 30% by weight relative to a total amount of the drug-containing particles.

[5] The masking particles according to any one of [1] to [4], wherein the carbonate is contained in an amount of 0.5 to 35% by weight relative to the total amount of the drug-containing particles.

[6] The masking particles according to any one of [1] to [5], wherein the carbonate is contained in an amount of 0.1 to 10 parts by weight relative to 1 part by weight of the acid.

[7] The masking particles according to any one of [1] to [6], wherein a content of the coating layer is 0.005 to 2 parts by weight relative to 1 part by weight of the drug-containing particles.

[8] The masking particles according to any one of [1] to [7], wherein the drug-containing particle is a uniform particle containing the drug, the acid, and the carbonate.

[9] The masking particles according to any one of [1] to [7], wherein the drug-containing particle comprises a portion containing the drug and a separate portion containing the acid and the carbonate.

[10] The masking particles according to [9], wherein the drug-containing particle comprises a core particle and an interlayer on the core particle, and
the core particle contains the drug, and the interlayer contains the acid and the carbonate, or
the core particle contains the acid and the carbonate, and the interlayer contains the drug.

[11] The masking particles according to [10], wherein the core particle contains a disintegrant.

[12] The masking particles according to [10] or [11], wherein the interlayer contains a binder and/or a fluidizer or lubricant.

[13] The masking particles according to any one of [1] to [7], wherein the drug-containing particle comprises a portion containing the acid and a separate portion containing the carbonate.

[14] The masking particles according to [13], wherein the drug-containing particle comprises a core particle and an interlayer on the core particle, the acid and the carbonate are separately contained in any of the core particle and the interlayer, and the drug is contained in the core particle, the interlayer, or both the core particle and the interlayer.

[15] The masking particles according to [14], wherein the core particle contains a disintegrant.

[16] The masking particles according to [14] or [15], wherein the interlayer contains a binder and/or a fluidizer or lubricant.

[17] The masking particles according to [13], wherein the drug-containing particle comprises a core particle, a first interlayer, and a second interlayer, and the drug, the acid, and the carbonate are separately contained in any of the core particle, the first interlayer, and the second interlayer.

[18] The masking particles according to [17], wherein the core particle contains a disintegrant.

[19] The masking particles according to [17] or [18], wherein one or both of the first interlayer and the second interlayer contain a binder and/or a fluidizer or lubricant.

[20] A tablet, granules, fine granules, or a powder comprising the masking particles according to any one of [1] to [19].

[21] An orally disintegrating tablet comprising the masking particles according to any one of [1] to [19].

[22] A method of controlling drug dissolution or drug release from drug-containing particles, the method comprising adding an acid and a carbonate to a particle containing a drug, and coating the drug-containing particle containing the drug, the acid, and the carbonate with a coating layer containing a water-insoluble polymer.

Advantageous Effects of Invention

In masking particles of the present invention, each particle containing a drug is coated with a coating layer containing a water-insoluble polymer, and thus the drug taste is not sensed or is suppressed in the mouth. Hence, the masking particles can be suitably used to produce a pharmaceutical composition containing a drug having an unpleasant taste such as bitterness.

The masking particles of the present invention can be suitably used as granules, fine granules, or powders, which are typical dosage forms likely to give the taste of a drug in the mouth, and the resulting preparation does not give or is unlikely to give the drug taste in the mouth.

The masking particles of the present invention can also be used to produce tablets. Even when the tablets produced by using the masking particles of the present invention are orally disintegrating tablet, the drug taste is not sensed or is unlikely to be sensed in the mouth because the particles containing the drug are coated. Tablets coated to suppress the drug taste are not typically made into orally disintegrating tablets, but using the masking particles of the present invention enables the production of orally disintegrating tablets that suppress the taste of a drug.

In the masking particles of the present invention, each particle containing a drug is coated with a coating layer containing a water-insoluble polymer, and thus drug release by contact with water in the oral cavity is suppressed. Accordingly, drug absorption from the oral cavity or pharynx is suppressed. This prevents unexpected side effects caused by the absorption of a drug from the oral cavity or pharynx and prevents variation in pharmaceutical effect among individuals.

The masking particles of the present invention suppress drug absorption from the oral cavity or pharynx and thus can be suitably used for the production of preparations soluble in the stomach or intestines.

After swallowing of the masking particles of the present invention, water in the digestive tract gradually infiltrates into the coating layer, and the water entering into the particles rapidly causes a reaction between an acid and a carbonate. The resulting foaming destroys the masking particles to release a drug. This mechanism enables sufficient absorption of a drug from the stomach or intestines (especially, the upper part of the small intestine). This mechanism also enables sufficient exertion of pharmaceutical effects of a drug targeting the stomach or intestines.

The masking particles of the present invention can release a drug at an intended time by adjusting the type of water-insoluble polymer, the thickness of the coating layer, the types and the amounts of the acid and the carbonate, the types and the amounts of other ingredients, the layer structure of the drug-containing particles, and other conditions. Hence, the drug release suppression time can be appropriately controlled in response to the type or the dosage form of a drug.

In the presence of water, an acid and a carbonate rapidly react to cause foaming, and thus the masking particles of the present invention can accurately control the drug release suppression time. This enables the production of a preparation having an intended drug release pattern depending on a drug or a dosage form.

DESCRIPTION OF EMBODIMENTS

Figure 1:
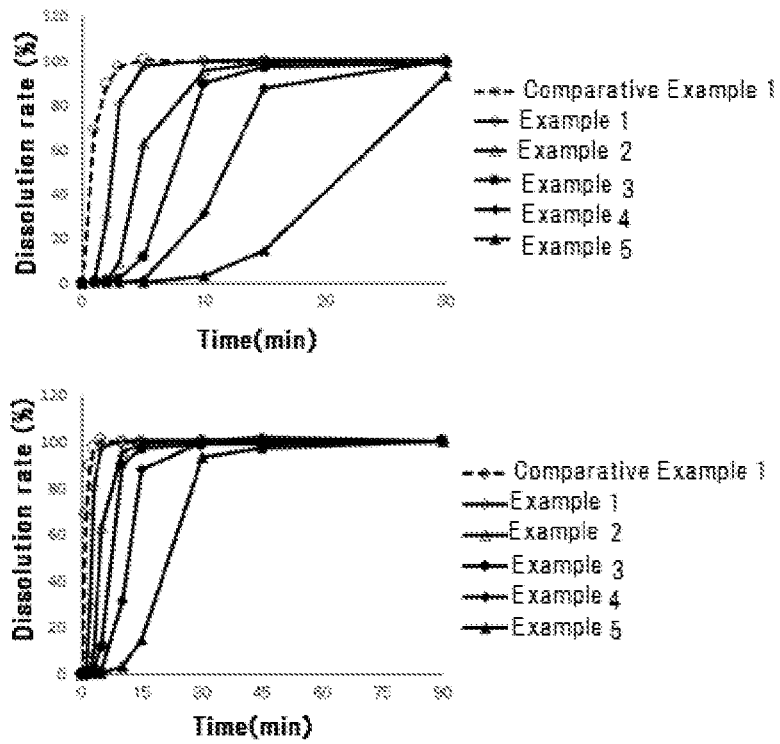
FIG. 1 is graphs showing the drug dissolution test results of masking particles each comprising a core particle containing a drug and an acid, an interlayer containing a carbonate, and a coating layer.

The present invention will now be described in detail.

Masking particles of the present invention are particles in which particles containing a drug, an acid, and a carbonate are each coated with a coating layer containing a water-insoluble polymer. The masking particles of the present invention can be used singly or be mixed with excipients to yield tablets, granules, fine granules, powders, or the like.

In the present invention, a granular portion containing a drug, an acid, and a carbonate is called a "drug-containing particle", and a particle prepared by coating the "drug-containing particle" with a coating layer containing a water-insoluble polymer is called a "masking particle". As described later, the granular portion containing a drug, an acid, and a carbonate (the portion except the coating layer) may be a particle having a uniform formula or may comprise a central core and an interlayer surrounding the central core. In each case, the portion except the coating layer is called a "drug-containing particle".

Acid

The acid can be any acid capable of reacting with a carbonate to generate carbon dioxide and also includes pharmaceutically acceptable acidic excipients and medicinally active acidic ingredients. Typically, an acidic substance having a lower pKa than that of carbonic acid can be used, and an organic acid, an inorganic acid, or a salt thereof is preferred. Examples of the organic acid include carboxylic acids such as acetic acid, fumaric acid, maleic acid, succinic acid, malonic acid, lactic acid, tartaric acid, citric acid, malic acid, ascorbic acid (vinyl carboxylic acid), glycolic acid, adipic acid, and carboxymethyl cellulose; sulfonic acids such as toluenesulfonic acid; amino acids; and glucono-δ-lactone. Examples of the organic acid salt include potassium tartrate. Examples of the inorganic acid include hydrochloric acid, nitric acid, sulfuric acid, and phosphoric acid. Examples of the inorganic acid salt include monocalcium phosphate. Of them, an organic acid is preferred, a carboxylic acid is more preferred, citric acid, tartaric acid, and malic acid are even more preferred, and citric acid is particularly preferred.

The acid may be a hydrate.

Acids may be used singly or in combination of two or more of them.

The content of the acid is preferably 1% by weight or more, more preferably 3% by weight or more, and even more preferably 5% by weight or more relative to the total amount of the drug-containing particles. The content is preferably 35% by weight or less, more preferably 25% by weight or less, and even more preferably 20% by weight or less. Within the above range, the acid can react with a carbonate to rapidly destroy masking particles in the stomach or intestines, and a drug can be released.

Carbonate

The carbonate may be any pharmaceutically acceptable carbonate, and examples of the water-soluble carbonate include sodium carbonate, potassium carbonate, sodium hydrogen carbonate, potassium hydrogen carbonate, and ammonium carbonate. Examples of the water-insoluble or poorly water-soluble carbonate include calcium carbonate and magnesium carbonate. Of them, a water-soluble carbonate is preferred, and a hydrogen carbonate is more preferred, and sodium hydrogen carbonate and potassium hydrogen carbonate are even more preferred.

Carbonates may be used singly or in combination of two or more of them.

The content of the carbonate is preferably 0.1% by weight or more, more preferably 3% by weight or more, and even more preferably 5% by weight or more relative to the total amount of the drug-containing particles. The content is preferably 35% by weight or less, more preferably 25% by weight or less, and even more preferably 20% by weight or less. Within the above range, the carbonate can react with an acid to rapidly destroy masking particles, and a drug can be released.

As for the content ratio of the carbonate to the acid, the content of the carbonate is preferably 0.1 part by weight or more, more preferably 0.3 part by weight or more, and even more preferably 0.5 part by weight or more relative to 1 part by weight of the acid. The content is preferably 10 parts by weight or less, more preferably 3 parts by weight or less, and even more preferably 1.5 parts by weight or less. Within the above range, the acid and the carbonate can cause foaming sufficient to achieve intended drug dissolution.

Drug

The drug may be any drug. Specifically preferred are a drug giving an unpleasant taste such as bitterness, acid taste, and irritating taste, a drug irritating the pharynx, and a drug absorbed from the oral cavity or pharynx.

Examples of the drug include hypolipidemic drugs (such as atorvastatin, pravastatin, simvastatin, and rosuvastatin), quinolone antimicrobials (such as moxifloxacin, gatifloxacin, sparfloxacin, tosufloxacin, sitafloxacin, levofloxacin, lomefloxacin, ciprofloxacin, fleroxacin, and garenoxacin), macrolide antibiotics (such as clarithromycin, azithromycin, roxithromycin, and erythromycin), non-steroidal anti-inflammatory drugs (such as aspirin, mefenamic acid, ibuprofen, naproxen, loxoprofen, and celecoxib), antihypertensive drugs (such as amlodipine, nifedipine, azilsartan, olmesartan medoxomil, irbesartan, losartan, candesartan cilexetil, and telmisartan), antidiabetics (such as metformin, miglitol, voglibose, nateglinide, mitiglinide, pioglitazone, sitagliptin, vildagliptin, alogliptin, linagliptin, anagliptin, saxagliptin, teneligliptin, ipragliflozin, dapagliflozin, canagliflozin, and empagliflozin), vasodilators (such as limaprost, beraprost, sildenafil, bosentan, hepronicate, kallidinogenase, and isoxsuprine), antidepressants (such as escitalopram, duloxetine, and paroxetine), antipsychotic drugs (such as olanzapine, quetiapine, clozapine, aripiprazole, risperidone, blonanserin, and perospirone), antianxiety drugs (such as clotiazepam, lorazepam, and diazepam), Alzheimer's dementia treatment drugs (such as donepezil, galantamine, rivastigmine, and memantine), antiepileptic drugs (such as levetiracetam, gabapentin, lamotrigine, zonisamide, carbamazepine, phenytoin, and valproic acid), neuropathic pain treatment drugs (such as pregabalin and mirogabalin), dopamine agonists (such as cabergoline, pramipexole, ropinirole, bromocriptine, pergolide, and amantadine), antihistamines (such as levocetirizine, cetirizine, epinastine, olopatadine, loratadine, desloratadine, rupatadine, ebastine, bepotastine, Zesulan (trade name), fexofenadine, ketotifen, emedastine, oxatomide, mequitazine, and azelastine), leukotriene inhibitors (such as montelukast, zafirlukast, and pranlukast), overactive bladder treatment drugs (such as solifenacin, imidafenacin, tolterodine, propiverine, flavoxate, clomipramine, imipramine, amitriptyline, mirabegron, and vibegron), cancer molecular target treatment agent (such as bortezomib), treatment drugs for dysuria accompanying benign prostatic hyperplasia (such as silodosin, chlormadinone, tamsulosin, and naftopidil), erectile dysfunction treatment drugs (such as tadalafil and vardenafil), insomnia treatment drugs (such as ramelteon, zolpidem, triazolam, nimetazepam, and quazepam), osteoporosis treatment drugs (such as risedronate sodium and alendronic acid), gout/hyperuricemia treatment drugs (such as febuxostat, topiroxostat, and allopurinol), hyperphosphatemia treatment drugs (such as lanthanum carbonate), salts thereof, and solvates thereof.

The content of the drug varies with the type of drug and is, for example, preferably 90% by weight or less relative to the total amount of the masking particles. The lower limit of the drug content varies with the drug and can be, for example, about 0.00001% by weight relative to the total amount of the masking particles.

Excipients

The masking particles of the present invention can contain, in the drug-containing particles, any excipients usable in tablets, granules, fine granules, powders, or the like as long as the effect of the invention is not impaired. Examples of the excipient include a diluent, a disintegrant, a binder, a lubricant or fluidizer (adhesion inhibitor), a coloring agent, a flavoring agent, a sweetening agent, and a preservative or antiseptic. Excipients may be used singly or in combination of two or more of them.

Examples of the diluent include sugars such as lactose hydrate, white soft sugar, maltose, fructose, glucose, and trehalose; sugar alcohols such as mannitol (especially, D-mannitol), maltitol, sorbitol, xylitol, erythritol, and lactitol; starches such as starch, pregelatinized starch, and partially pregelatinized starch; celluloses such as crystalline cellulose; dextrin; dextran; glycerol fatty acid esters; and inorganic powders such as magnesium aluminometasilicate and synthetic hydrotalcite.

Examples of the binder include povidone; celluloses such as methyl cellulose, ethyl cellulose, carboxymethyl cellulose, hydroxypropyl cellulose, hydroxyethyl cellulose, hydroxypropyl methyl cellulose (hypromellose), and croscarmellose sodium; starch; gelatin; polysaccharide thickeners such as agar, alginic acid, sodium alginate, tragacanth, xanthan gum, gum arabic, pullulan, and dextrin; polyvinyl alcohol-polyethylene glycol graft copolymers; carboxyvinyl polymers; polyethylene oxide; copolyvidone; polyoxyethylene hydrogenated castor oil; polymers containing a derivative in which a hydrophobic group is introduced to the N-position of N-isopropyl acrylamide and/or acrylamide; polyoxyethylene-polyoxypropylene glycol; polyvinyl alcohols (including partially saponified polyvinyl alcohols); basic (meth)acrylate copolymers; and polyethylene glycol.

Examples of the disintegrant include crospovidone; celluloses such as carboxymethyl cellulose (carmellose), carmellose sodium, carmellose calcium, low-substituted hydroxypropyl cellulose, croscarmellose sodium, and crystalline cellulose; starches such as starch, pregelatinized starch, partially pregelatinized starch, sodium carboxymethyl starch, sodium carboxy starch, and hydroxypropyl starch; dextrin; calcium silicate; calcium citrate; and light anhydrous silicic acid.

Examples of the lubricant or fluidizer (adhesion inhibitor) include stearic acid, stearates (such as magnesium stearate, calcium stearate, aluminum stearate, and zinc stearate), sodium stearyl fumarate, glycerylmonostearate, glyceryl palmitostearate, sodium lauryl sulfate, polyethylene glycol, talc, glycerol fatty acid esters, sucrose fatty acid esters, sodium potassium tartrate, carnauba wax, L-leucine, polyethylene glycol, hardened oil, silicic acid compounds (such as light anhydrous silicic acid, magnesium aluminometasilicate, hydrated silicon dioxide, and synthetic aluminum silicate), and titanium oxide.

Examples of the coloring agent include yellow ferric oxide, red ferric oxide, titanium oxide, black iron oxide, edible tar dyes, natural pigments (such as β-carotene and riboflavin).

Examples of the sweetening agent include sucralose, mannitol, sucrose, aspartame, *stevia*, and acesulfame potassium.

Examples of the preservative or antiseptic include ethyl p-hydroxybenzoate, propyl p-hydroxybenzoate, butyl p-hydroxybenzoate, benzoic acid, and sodium benzoate.

Coating Layer

The coating layer contains a water-insoluble polymer usable as the coating agent in pharmaceutical preparations. In the present invention, the "water-insoluble polymer" includes polymers poorly soluble in water, in addition to polymers completely insoluble in water.

Examples of the water-insoluble polymer include cellulose coating agents (such as methyl cellulose, ethyl cellulose, hydroxyethyl cellulose, carboxymethyl ethyl cellulose, sodium carboxymethyl cellulose, hypromellose phthalate, hypromellose acetate succinate, cellulose acetate, and cellulose acetate phthalate), vinyl polymers (such as polyvinyl acetal diethylamino acetate and polyvinyl acetate phthalate), methacrylate polymers or methacrylic acid polymers, and polysiloxane coating agents (such as dimethylpolysiloxane and dimethylpolysiloxane-silicon dioxide mixtures).

Of them, a methacrylate polymer or methacrylic acid polymer and a cellulose coating agent (especially, ethyl cellulose) are preferred, and a methacrylate polymer or methacrylic acid polymer is more preferred.

The methacrylate polymer or methacrylic acid polymer is available as various commercial products, and examples include EUDRAGIT E series, EUDRAGIT L series, EUDRAGIT S series, EUDRAGIT R series, EUDRAGIT NE series, and EUDRAGIT FS series (registered trademark) manufactured by Roehm GmbH. Specific examples include aminoalkyl methacrylate copolymer E (such as EUDRAGITs E100 and EPO), methacrylic copolymer LD (such as EUDRAGITs L30D-55 and L100-55), methacrylic acid copolymer L (such as EUDRAGIT L100), methacrylic acid copolymer S (such as EUDRAGIT S100), ammonioalkyl methacrylate copolymer (such as EUDRAGITs RL100, RLPO, RS100, RSPO, RL30D, and RS30D), and ethyl acrylate-methyl methacrylate copolymer (such as EUDRAGIT NE30D).

The water-insoluble polymer is classified, for example, into pH-independent polymers, enteric polymers, and gastro-soluble polymers. In the present invention, any water-insoluble polymer can be preferably used and can be selected so as to achieve an intended release suppression time for a drug. As described in a section in examples, in the masking particles of the present invention, water gradually infiltrates through the coating layer to cause the reaction between an acid and a carbonate, and the resulting foaming destroys the masking particles. For example, even when an enteric polymer is used, this mechanism also enables the dosage form design to release a drug before the masking particles reach the intestines.

The coating layer can contain excipients such as a plasticizer, a binder, a fluidizer or lubricant (adhesion inhibitor), a coloring agent, and a sweetening agent as long as the effect of the invention is not impaired. Excipients may be used singly or in combination of two or more of them.

Examples of the plasticizer include glycerol fatty acid esters such as polyethylene glycol, propylene glycol, glycerol, and triacetin (glycerol triacetate), liquid paraffin, sorbitan monolaurate, monostearin, triethyl citrate, tributyl citrate, diethyl phthalate, dibutyl phthalate, diethyl sebacate, dibutyl sebacate, poloxamer, and polyoxyethylene hydrogenated castor oil.

Examples of the binder, the fluidizer or lubricant (adhesion inhibitor), the coloring agent, and the sweetening agent include those exemplified as the excipients for the drug-containing particles.

The content of the coating layer is preferably 0.01 part by weight or more, more preferably 0.05 part by weight or more, and even more preferably 0.1 part by weight or more relative to 1 part by weight of the drug-containing particles. The content is preferably 1 part by weight or less, more preferably 0.5 part by weight or less, and even more preferably 0.3 part by weight or less. Within the above range, water infiltrates at an appropriate speed, the drug release in the oral cavity or at the pharynx is sufficiently suppressed, and subsequently, the drug can be rapidly released.

Particle Structure

In the masking particles of the present invention, each drug-containing particle containing a drug, an acid, and a carbonate is at least coated with a coating layer containing a water-insoluble polymer, and the particle can have various structures.

First Embodiment

The masking particles can be, for example, particles in which each uniform or single-structure drug-containing particle containing a drug, an acid, and a carbonate is coated with a coating layer. In the embodiment, an acid and a carbonate are contained in the same portion, and thus water infiltrating through the coating layer can very rapidly cause foaming to release a drug. The drug-containing particles can further contain any excipients usable in tablets, granules, fine granules, powders, or the like.

Second Embodiment

The masking particles can be particles in which each drug-containing particle comprising a portion containing a drug and a separate portion containing an acid and a carbonate is coated with a coating layer.

For example, each drug-containing particle consisting of a core particle and a covering layer thereon (the layer is between the core particle and the coating layer and thus is also called "interlayer") is coated with a coating layer to give a particle. The core particle contains a drug, and the interlayer contains an acid and a carbonate. Alternatively, the core particle contains an acid and a carbonate, and the interlayer contains a drug.

When the core particle contains a drug, the core particle can consist of a central core containing a diluent or the like and a drug-containing layer surrounding the central core. This structure facilitates the production of spherical drug-containing particles. Accordingly, the coating layer is easily formed, and drug-containing particles having a narrow particle size distribution can be produced.

Between the core particle and the interlayer, another interlayer containing a diluent or the like can also be provided.

In the embodiment, an acid and a carbonate are contained separately from a drug, and this facilitates the use of a drug susceptible to acid or alkali. An acid and a carbonate are contained in the same portion, and thus water infiltrating through the coating layer can very rapidly cause foaming to release a drug.

In the embodiment, the core particle and the interlayer can further contain any excipients usable in granules, fine granules, powders, or the like.

Specifically, when the core particle contains a disintegrant, the water absorbability of the disintegrant facilitates water infiltration, and thus an acid and a carbonate readily react. The disintegrant is preferably crospovidone or a cellulose such as carboxymethyl cellulose (carmellose), carmellose sodium, carmellose calcium, low-substituted hydroxypropyl cellulose, and crystalline cellulose and is more preferably low-substituted hydroxypropyl cellulose. The content of the disintegrant is preferably about 0.5 to 50% by weight relative to the total amount of the drug-containing particles.

The interlayer preferably contains a binder to facilitate the layer formation. The binder is preferably hydroxypropyl cellulose, hydroxypropyl methyl cellulose (hypromellose), or polyethylene glycol. The content of the binder is preferably about 0.1 to 20% by weight relative to the total amount of the drug-containing particles.

The interlayer preferably contains a fluidizer or lubricant (adhesion inhibitor) to suppress the electrification of particles for a smooth production process. The content of the fluidizer or lubricant in the interlayer is preferably about 0.01 to 50% by weight relative to the total amount of the drug-containing particles.

Third Embodiment

The masking particles can be particles in which each drug-containing particle comprising a portion containing an acid and a separate portion containing a carbonate is coated with a coating layer.

An acid and a carbonate contained in the same portion causes foaming when dissolved. Hence, water cannot be used in the production process, and the production method may be limited. To address this disadvantage, for example, a drug-containing particle consisting of a core particle and an interlayer can be coated with a coating layer to give a granular composition, and an acid and a carbonate can be separately contained in any of the core particle and the interlayer. In this case, the acid and the carbonate are separately present in different portions, and thus one or both of the core particle and the interlayer can be formed by using water. In particular, an interlayer material can be used as an aqueous solution for coating (interlayer formation).

The acid and the carbonate may be contained in any of the core particle and the interlayer. Preferred are particles in which the core particle contains an acid, and the interlayer contains a carbonate because, for example, this facilitates the use of a coating layer unstable to acid.

The drug is at least contained in one or both of the core particle and the interlayer. When the acid and the drug are separately contained, a drug susceptible to acid is easily used, and when the carbonate and the drug are separately contained, a drug susceptible to alkali is easily used.

In the embodiment, the core particle and the interlayer can further contain any excipients usable in granules, fine granules, powders, or the like. The core particle preferably contains a disintegrant, and the interlayer preferably contains a binder and a fluidizer or lubricant (adhesion inhibitor). Preferred types and contents of the disintegrant, the binder, and the fluidizer or lubricant (adhesion inhibitor) are as described for the core particle and the interlayer in the second embodiment.

In the third embodiment, the drug, the acid, and the carbonate can be separately contained in different portions. In this case, the acid and the carbonate are separately present in different portions, and this eliminates the necessity of limited use of water or the like in production processes. In addition, the drug is separately present from the acid and the carbonate in a different portion, and this facilitates the use of a drug susceptible to acid or alkali.

For example, a drug-containing particle consisting of a core particle and two interlayers covering the core particle is coated with a coating layer to give a particle, and any of the core particle, the inside interlayer (hereinafter also called "first interlayer"), and the outside interlayer (hereinafter also called "second interlayer") may contain a drug, an acid, or a carbonate, separately. Preferably, the core particle contains a drug, and the two interlayers can separately contain an acid and a carbonate. The first interlayer and the second interlayer can separately contain an acid and a carbonate interchangeably, but the first interlayer preferably contains an acid, and the second interlayer preferably contains a carbonate. The core particle can consist of a central core containing a diluent or the like and a drug-containing layer surrounding the central core. Between the portion (or the layer) containing a drug and the portion (or the layer) containing an acid or a carbonate, another interlayer containing a diluent or the like can be provided. In this case, the outer layer of the core particle may also be called a first interlayer, the layer outside the first interlayer may also be called a second interlayer, and the layer outside the second interlayer may also be called a third interlayer.

In the embodiment, the core particle and the interlayers can further contain any excipients usable in tablets, granules, fine granules, powders, or the like. The core particle preferably contains a disintegrant, and the preferred type and content of the disintegrant are as described for the core particle in the second embodiment. Each interlayer preferably contains a binder and a fluidizer or lubricant (adhesion inhibitor), and the preferred types of the binder and the fluidizer or lubricant (adhesion inhibitor) are as described for the interlayer in the second embodiment. When each interlayer contains a binder, the total content of the binder is preferably 0.1 to 20% by weight relative to the total amount of the drug-containing particles. When each interlayer contains a fluidizer or lubricant (adhesion inhibitor), the total content of the fluidizer or lubricant is preferably 0.01 to 50% by weight relative to the total amount of the drug-containing particles.

The masking particles of the present invention can be particles having various structures in addition to the first to third embodiments.

Production Method

In the masking particles of the present invention, the drug-containing particles, the core particles, and the central cores containing a diluent can be produced in a common procedure by wet or dry granulation and as needed by drying and rounding. Examples of the wet granulation include fluidized-bed granulation, agitation granulation, tumbling granulation, extrusion granulation, crushing granulation, kneading granulation, continuous direct granulation, and complex fluidized-bed granulation. Examples of the dry granulation include dry complex granulation, roller compaction dry granulation, briquette granulation, and melt granulation.

The interlayer and the coating layer can be produced in a common procedure by using a machine such as a fluidized-bed coating machine, a Wurster fluidized-bed coating machine, a centrifugal fluidized-bed coating machine, and a tumbling fluidized-bed coating machine.

Properties

The drug-containing particle containing a drug, an acid, and a carbonate has various shapes depending on granulation methods and can be spherical, cylindrical, prolate spherical (prolate elliptic), or the like.

The particle size of the masking particles after coating with the coating layer is not limited to particular values, and the $D_{50}$ can be about 50 to 1,000 µm, specifically about 100 to 800 µm. The $D_{50}$ can be 50 µm or more, 100 µm or more, 200 µm or more, or 300 µm or more and can be 1,000 µm or less, 800 µm or less, 600 µm or less, or 400 µm or less. In the present invention, the $D_{50}$ is a particle size measured and calculated in accordance with the particle size determination by laser diffractometry in the particle size determination described in the Japanese Pharmacopoeia, Seventeenth Edition, and is specifically a value determined by the method described in a section in EXAMPLES.

Tablets

The masking particles of the present invention can be used to produce tablets. Accordingly, the present invention also provides a tablet produced by using the masking particles of the present invention. The tablet can be produced, for example, by directly tableting the masking particles of the present invention or by tableting a mixture with one or more excipients.

The masking particles of the present invention mask a drug taste sensed in the mouth and thus can be suitably used to produce orally disintegrating tablets. Various methods of producing the orally disintegrating tablet are known, and a person skilled in the art can produce orally disintegrating tablets by appropriately selecting the types and the amounts of excipients to be mixed with the masking particles of the present invention.

When the masking particles of the present invention are mixed with excipients to produce an orally disintegrating tablet, the content of the masking particles of the present invention can be 1% by weight or more, 5% by weight or more, or 10% by weight or more relative to the total amount of the orally disintegrating tablet. The content can be 90% by weight or less, 70% by weight or less, or 60% by weight or less.

Drug Dissolution Rate

The masking particles of the present invention have various dissolution rates depending on the type of drug, but the dissolution rate determined by using a pH 6.8 dissolution test solution in accordance with the paddle method in the dissolution test described in the Japanese Pharmacopoeia, Seventeenth Edition, is preferably substantially 0 (substantially no drug is dissolved) for at least 0.5 minute, specifically for at least 1 minute, specifically for at least 1.5 minutes, or specifically for at least 3 minutes after the start of the test.

The masking particles of the present invention can have a drug release lag time of 0.5 minute or more, 1 minute or more, or 3 minutes or more. The drug release lag time can be 15 minutes or less, 10 minutes or less, or 8 minutes or less. The drug release lag time is a value determined by the method described in a section in examples.

The masking particles of the present invention preferably have a drug release rate of 1%/min or more, specifically 2%/min or more, specifically 10%/min or more, or specifically 30%/min or more. The drug release rate can be 80%/min or less, 70%/min or less, or 60%/min or less. The drug release rate is a value determined by the method described in a section in EXAMPLES.

Drug Dissolution Control Method

The present invention encompasses a method of delaying drug dissolution or drug release from drug-containing particles for a predetermined period of time, or a method of suppressing drug dissolution or drug release for a predetermined period of time, by adding an acid and a carbonate to a particle containing a drug and by coating the drug-containing particle containing the drug, the acid, and the carbonate with a coating layer containing a water-insoluble polymer. By the method, the drug dissolution suppression time can be controlled by selecting the types, amounts, and ratios of the acid, the carbonate, and other ingredients contained in the drug-containing particles; the amount of the coating layer; the types, amounts, and ratios of ingredients contained in the coating layer; and other conditions. The types, amounts, and ratios of the acid, the carbonate, and other ingredients contained in the drug-containing particles; the amount of the coating layer; the types, amounts, and ratios of ingredients contained in the coating layer; and other conditions are as described for the masking particles of the present invention. The present invention therefore encompasses a method of controlling drug dissolution or drug release from drug-containing particles by adding an acid and a carbonate to a particle containing a drug and by coating the drug-containing particle containing the drug, the acid, and the carbonate with a coating layer containing a water-insoluble polymer.

EXAMPLES

The present invention will next be described in further detail with reference to examples, but the present invention is not limited to them.

(1) Test Method (Dissolution Test)

Dissolution test was performed in accordance with the second method of the dissolution test described in the Japanese Pharmacopoeia. The paddle rotation rate was set at 50 rpm, and 900 mL of a pH 6.8 phosphate buffer solution (the second solution of the disintegration test in the Japanese Pharmacopoeia) was used as the test solution. Drug-containing particles, masking particles, or tablets containing 250 mg of levofloxacin were placed in a vessel. At testing times of 1, 2, 3, 5, 10, 15, 30, 45, and 90 minutes, 10 mL of the solution was sampled from each vessel, and the dissolution rate was determined by ultraviolet-visible spectrophotometry. The measurement was repeated three times, and the average was calculated as an average dissolution rate.

(Particle Size Distribution Measurement)

In the present invention, the particle size was determined by using a laser diffraction particle size analyzer (manufactured by Malvern) based on volume.

(2) Effect of Coating Layer

Examples 1 to 5

Drug-containing particles each comprising a core particle containing levofloxacin hydrate and citric acid hydrate and an interlayer containing a sodium hydrogen carbonate and masking particles prepared by coating the drug-containing particles were produced by the following procedures.

[Preparation of Core Particles]

In an agitation mixing granulator (manufactured by Powrex; Vertical granulator FM-VG-05, hereinafter the same applies), 400 g of levofloxacin hydrate, 240 g of pulverized citric acid hydrate (manufactured by Satuma Kako, hereinafter the same applies), and 160 g of low-substituted hydroxypropyl cellulose (manufactured by Shin-Etsu Chemical; LHPC31, hereinafter the same applies) were placed and mixed, and then 560 g of purified water was sprayed while the mixture was stirred, giving a kneaded mixture.

Next, the kneaded mixture was extrusion-granulated by using a wet extrusion granulator, Multigran (manufactured by DALTON; MG-55-2, hereinafter the same applies), and the resulting particles were rounded by using a spherical granulator, Marumerizer (manufactured by DALTON; QJ-230T-2, hereinafter the same applies). The product was then sieved, and particles passed through a 30-mesh (500 μm) sieve but not passed through a 42-mesh (355 μm) sieve were collected as core particles.

[Preparation of Coating Liquid for Interlayer (1)]

To a solution of 12 g of hydroxypropyl cellulose (manufactured by Nippon Soda; HPCL, hereinafter the same applies) in 400 g of absolute ethanol (manufactured by Japan Alcohol, hereinafter the same applies), 25 g of talc (manufactured by Hayashi-Kasei; Talcan Hayashi, hereinafter the same applies) and 45 g of pulverized sodium hydrogen carbonate (manufactured by AGC, hereinafter the same applies) were added, and the whole was stirred to give an interlayer-forming coating liquid (1).

[Preparation of Drug-Containing Particles]

In a tumbling fluidized-bed coating machine (manufactured by Powrex; Multiplex, hereinafter the same applies), 150 g of the resulting core particles were placed, and the coating liquid (1) was sprayed to give drug-containing particles coated with 82 g of an interlayer.

[Preparation of Coating Liquid for Masking (2)]

In a mixed liquid of 270 g of ethanol and 30 g of purified water, 30 g of aminoalkyl methacrylate copolymer E (manufactured by Evonik Nutrition & Care GmbH; EUDRAGIT E, hereinafter the same applies) was dissolved, and 30 g of talc was added. The whole was stirred to give a coating liquid for masking (2).

[Preparation of Masking Particles]

In a tumbling fluidized-bed coating machine, 200 g of the resulting drug-containing particles were placed, and the coating liquid (2) was sprayed to give masking particles.

Relative to the mass of the drug-containing particles, particles having a masking-layer (a coating layer containing a water-insoluble polymer is called a masking layer, the same applies hereinafter) at a mass ratio of 6% were regarded as Example 1, particles having a masking layer at a mass ratio of 125 were regarded as Example 2, particles having a masking layer at a mass ratio of 18% were regarded as Example 3, particles having a masking layer at a mass ratio of 24% were regarded as Example 4, and particles having a masking layer at a mass ratio of 30% were regarded as Example 5.

Comparative Example 1

A similar procedure to that for Examples 1 to 5 was performed, giving drug-containing particles as Comparative Example 1.

Masking particles of Examples 1 to 5 and drug-containing particles of Comparative Example 1 were subjected to the dissolution test. Changes in dissolution rate of levofloxacin hydrate are shown in FIG. 1. The upper graph in FIG. 1 shows the results for 30 minutes after the start of the test, and the lower graph shows the results for 90 minutes after the start of the test.

In Comparative Example 1, the drug release was rapid by foaming, but no drug release lag time was observed because the particles lacked the coating layer containing a water-insoluble polymer. In contrast, in Examples 1 to 5, the coating layer containing a water-insoluble polymer prevented water infiltration for a certain period of time, and then water infiltrated. The resulting foaming caused membrane disruption from the inside to rapidly release the drug. As a result, lag times of 1 to 5.9 minutes and rapid drug release rates of 2.3 to 50.9%/min were satisfied.

The drug release lag time is a time until 1a of a drug is released in a dissolution test at pH 6.8 and was calculated from two measurement time points between which 1% was interposed.

The drug release rate was calculated from the first two measurement time points of dissolution rate measurement within a dissolution rate of 3 to 90% in the dissolution test at pH 6.8.

(3) Effect of Acid

Comparative Example 2

The same procedure as in Comparative Example 1 was performed except that erythritol (manufactured by B Food Science; erythritol 100M, hereinafter the same applies) was used in place of citric acid hydrate, giving drug-containing particles as Comparative Example 2.

Comparative Example 3

In a tumbling fluidized-bed coating machine, 190 g of the drug-containing particles of Comparative Example 2 were placed, and the coating liquid (2) was sprayed to give masking particles. The particles had a masking layer at a mass ratio of 18% relative to the mass of the drug-containing particles, as with Example 3.

Comparative Example 3 was the same as Example 3 except that erythritol was used in the core particles in place of citric acid hydrate in Example 3.

Figure 2:
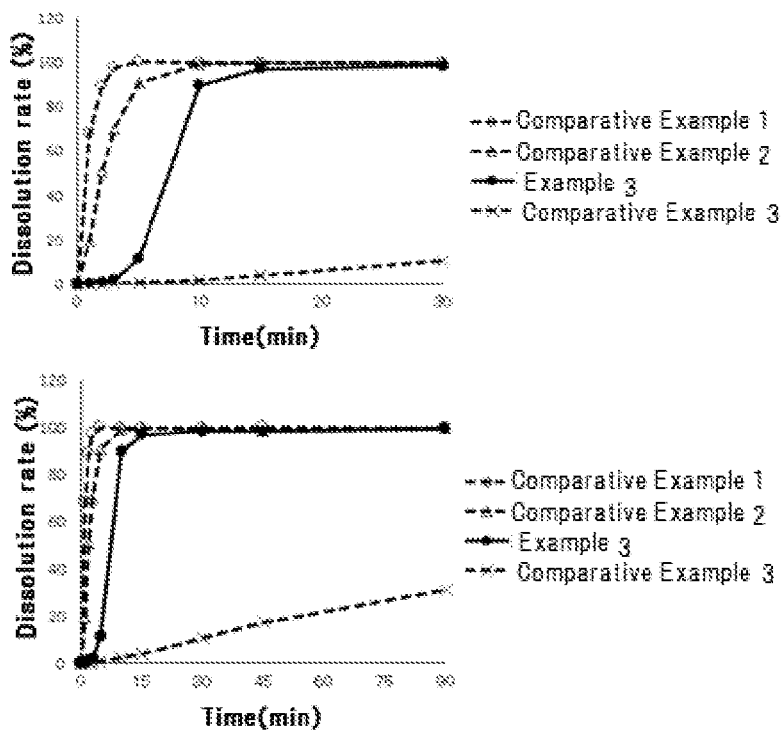
FIG. 2 is graphs comparing the drug dissolution between drug-containing particles containing an acid and drug-containing particles containing no acid.

The masking particles of Example 3, the drug-containing particles of Comparative Example 2, and the masking particles of Comparative Example 3 were subjected to the dissolution test. Changes in dissolution rate of levofloxacin hydrate are shown in FIG. 2. The upper graph in FIG. 2 shows the results for 30 minutes after the start of the test, and the lower graph shows the results for 90 minutes after the start of the test.

In Comparative Example 2, the drug release was rapid as with Comparative Example 1, but no lag time was observed because the particles lacked the coating layer containing a water-insoluble polymer.

In Comparative Example 3, a lag time of 6.5 minutes was observed due to the coating layer containing a water-insoluble polymer, but membrane disruption by foaming was not caused, and thus the drug was released with gradual diffusion. As a result, the drug release rate was slow, and the drug was insufficiently eluted even at 90 minutes after the start of the test.

The results reveal that an acid is essential for the rapid drug release after the drug release suppression.

(4) Type of Water-Insoluble Polymer in Coating Layer

Examples 6 and 7

[Preparation of Coating Liquid for Masking (3)]

In a mixed liquid of 720 g of ethanol and 80 g of purified water, 40 g of ethyl cellulose (manufactured by THE DOW CHEMICAL; ETHOCEL Standard 7 Premium, hereinafter the same applies) was dissolved, and 40 g of talc was added. The whole was stirred to give a coating liquid (3).
[Preparation of Masking Particles]

In a tumbling fluidized-bed coating machine, 200 g of the drug-containing particles of Comparative Example 1 were placed, and the coating liquid (3) was sprayed to give masking particles.

Relative to the mass of the drug-containing particles, particles having a masking layer at a mass ratio of 9, were regarded as Example 6, and particles having a masking layer at a mass ratio of 12% were regarded as Example 7.

Figure 3:
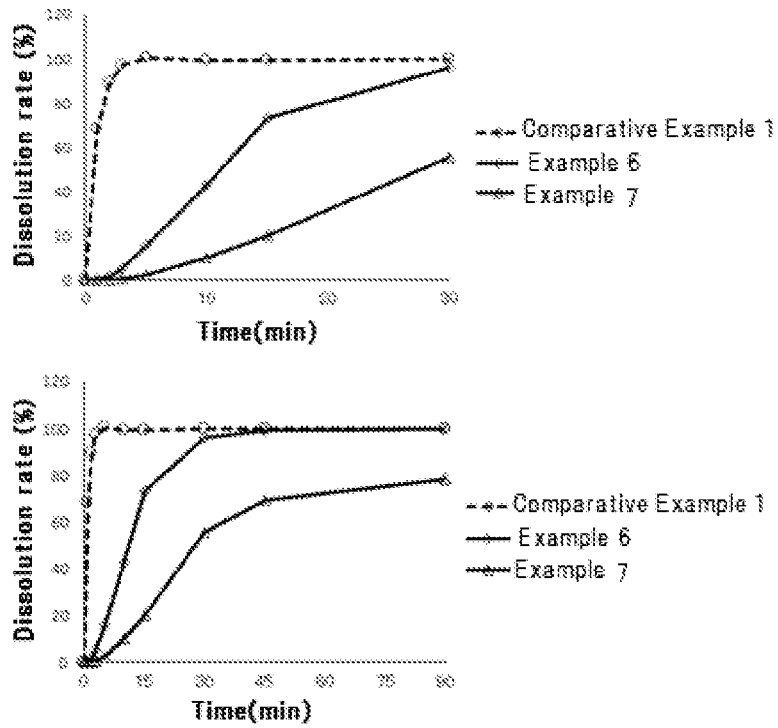
FIG. 3 is graphs showing the drug dissolution test results of masking particles each comprising a core particle containing a drug and an acid, an interlayer containing a carbonate, and a coating layer, and the coating layer contains a water-insoluble polymer different from that in the masking particles in FIG. 1.

The masking particles of Examples 6 and 7 were subjected to the dissolution test. Changes in dissolution rate of levofloxacin hydrate are shown in FIG. 3. The upper graph in FIG. 3 shows the results for 30 minutes after the start of the test, and the lower graph shows the results for 90 minutes after the start of the test.

In Examples 6 and 7, the coating layer containing a water-insoluble polymer prevented water infiltration for a certain period of time, and then water infiltrated. The resulting foaming caused membrane disruption from the inside to rapidly release the drug. As a result, lag times of 1.4 to 5.4 minutes and rapid drug release rates of 3.7 to 5.1%/min were satisfied.

The water-soluble polymer in the coating layers of Examples 6 and 7 was ethyl cellulose, which differs from aminoalkyl methacrylate copolymers E in Examples 1 to 5. In Examples 6 and 7, after the lag time, gradual drug release rates were observed as compared with Examples 1 to 5.

The results reveal that the drug release suppression for a certain period of time and the subsequent rapid drug release can be achieved, independent of the type of water-insoluble polymer. The results also reveal that the drug release suppression time and the subsequent drug release rate can be controlled by selecting the type of water-insoluble polymer.

(5) Amounts of Acid and Carbonate

Examples 8 to 11

[Preparation of Core Particles]

In an agitation mixing granulator, 422.5 g of levofloxacin hydrate, 97.5 g of pulverized citric acid hydrate, and 130 g of low-substituted hydroxypropyl cellulose were placed and mixed, and then 565.5 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.
[Preparation of Drug-Containing Particles]

In a tumbling fluidized-bed coating machine, 200 g of the resulting core particles were placed, and the coating liquid (1) was sprayed to give drug-containing particles coated with 54.7 g of an interlayer.
[Preparation of Masking Particles]

In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 12% were regarded as Example 8, particles having a masking layer at a mass ratio of 18% were regarded as Example 9, particles having a masking layer at a mass ratio of 24% were regarded as Example 10, and particles having a masking layer at a mass ratio of 30% were regarded as Example 11.

Comparative Example 4

A similar procedure to that for Examples 8 to 11 was performed, giving drug-containing particles as Comparative Example 4.

Examples 12 to 15

[Preparation of Core Particles]

In an agitation mixing granulator, 487.5 g of levofloxacin hydrate, 32.5 g of pulverized citric acid hydrate, and 130 g of low-substituted hydroxypropyl cellulose were placed and mixed, and then 560 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]

In a tumbling fluidized-bed coating machine, 150 g of the resulting core particles were placed, and the coating liquid (1) was sprayed to give drug-containing particles coated with 13.7 g of an interlayer.

[Preparation of Masking Particles]

In a tumbling fluidized-bed coating machine, 150 g of the resulting drug-containing particles were placed, and the coating liquid (2) was sprayed to give masking particles.

Relative to the mass of the drug-containing particles, particles having a masking layer at a mass ratio of 12% were regarded as Example 12, particles having a masking layer at a mass ratio of 18% were regarded as Example 13, particles having a masking layer at a mass ratio of 24% were regarded as Example 14, and particles having a masking layer at a mass ratio of 30% were regarded as Example 15.

Comparative Example 5

A similar procedure to that for Examples 12 to 15 was performed, giving drug-containing particles as Comparative Example 5.

Figure 4:
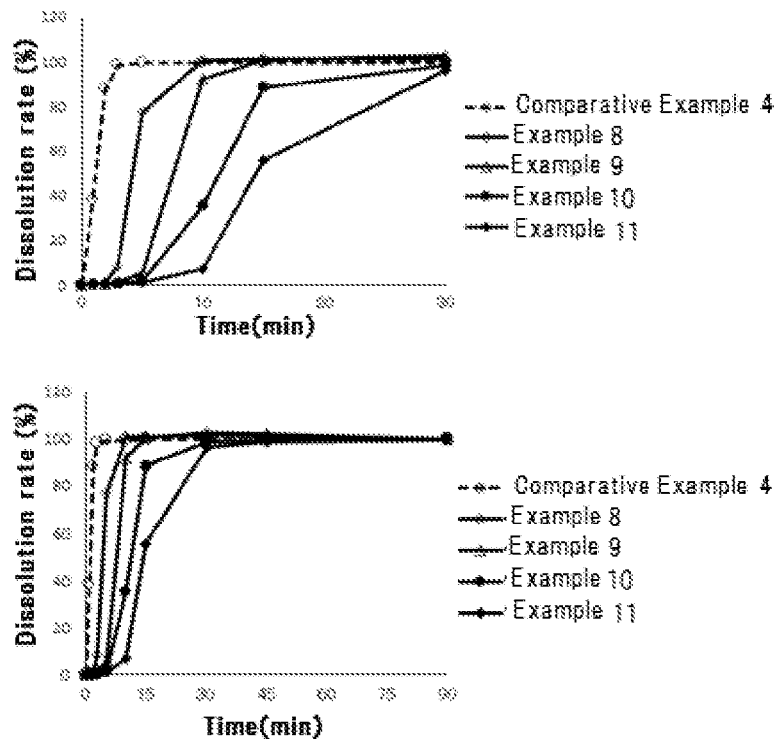
FIG. 4 is graphs showing the drug dissolution test results of masking particles each comprising a core particle containing a drug and an acid, an interlayer containing a carbonate, and a coating layer, and the contents of the acid and the carbonate are less than those in the masking particles in FIG. 1.
Figure 5:
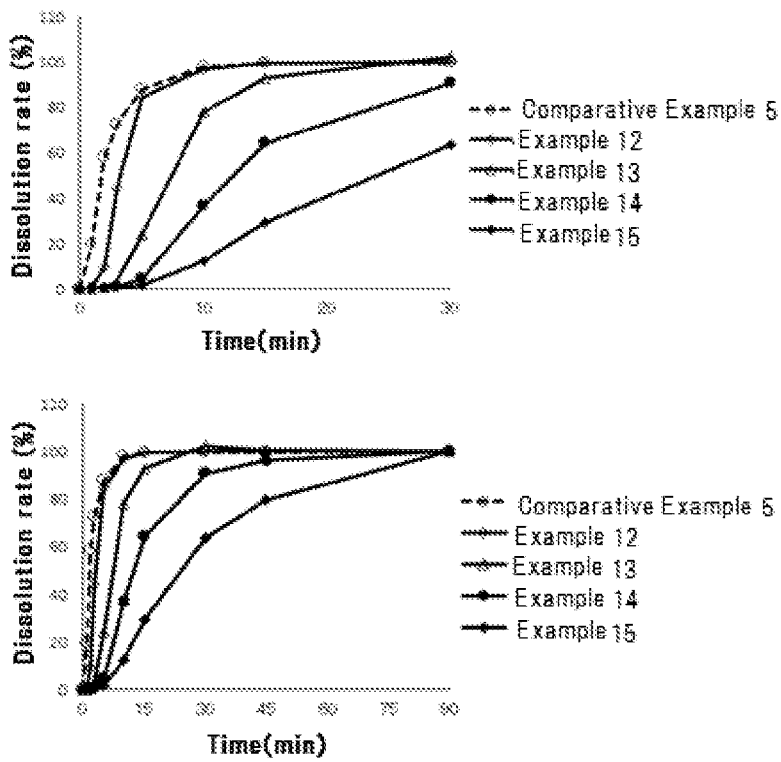
FIG. 5 is graphs showing the drug dissolution test results of masking particles each comprising a core particle containing a drug and an acid, an interlayer containing a carbonate, and a coating layer, and the contents of the acid and the carbonate are less than those in the masking particles in FIG. 4.

The masking particles of Examples 8 to 11, the drug-containing particles of Comparative Example 4, the masking particles of Examples 12 to 15, and the drug-containing particles of Comparative Example 5 were subjected to the dissolution test. Changes in dissolution rate of levofloxacin hydrate from the masking particles of Examples 8 to 11 and from the drug-containing particles of Comparative Example 4 are shown in FIG. 4, and changes in dissolution rate from the masking particles of Examples 12 to 15 and from the drug-containing particles of Comparative Example 5 are shown in FIG. 5. The upper graphs in FIGS. 4 and 5 show the results for 30 minutes after the start of the test, and the lower graphs show the results for 90 minutes after the start of the test.

In Examples 1 to 5, the content of citric acid hydrate is 153.8 mg, and the content of sodium hydrogen carbonate is 153.8 mg. In contrast, in Examples 8 to 11, the content of citric acid hydrate was as small as 59.1 mg, and the content of sodium hydrogen carbonate was as small as 59.1 mg. In Examples 12 to 15, the content of citric acid hydrate was as smaller as 17.1 mg, and the content of sodium hydrogen carbonate was as smaller as 17.1 mg.

In Comparative Examples 4 and 5, the drug release was rapid by foaming, but no lag time was observed because the particles lacked the coating layer containing a water-insoluble polymer.

In contrast, in Examples 8 to 11 and Examples 12 to 15, the coating layer containing a water-insoluble polymer prevented water infiltration for a certain period of time, and then water infiltrated. The resulting foaming caused membrane disruption from the inside to rapidly release the drug. As a result, in Examples 8 to 11, lag times of 1 to 4.2 minutes and rapid drug release rates of 9.7 to 34.5%/min were satisfied. In Examples 12 to 15, lag times of 1 to 3.4 minutes and rapid drug release rates of 3.5 to 34.3%/min were satisfied.

The results reveal that the drug release suppression for a certain period of time and the subsequent rapid drug release can be achieved even when the contents of an acid and a carbonate are varied in a wide range of amounts. The results also reveal that the drug release suppression time and the drug release rate can be controlled by adjusting the amounts of an acid and a carbonate.

(6) Type of Binder

Example 16

[Preparation of Coating Liquid for Interlayer (4)]

To a solution of 12 g of polyethylene glycol (Sanyo Chemical Industries; macrogol 6000, hereinafter the same applies) in 171 g of absolute ethanol, 25 g of talc and 45 g of pulverized sodium hydrogen carbonate were added, and the whole was stirred to give a coating liquid (4).

[Preparation of Drug-Containing Particles]

In a tumbling fluidized-bed coating machine, 150 g of the same core particles as those of Examples 1 to 5 and Comparative Example 1 were placed, and the coating liquid (4) was sprayed to give drug-containing particles coated with 82 g of an interlayer.

[Preparation of Masking Particles]

In a tumbling fluidized-bed coating machine, 190 g of the resulting drug-containing particles were placed, and the coating liquid (2) was sprayed to give masking particles. The particles had a masking layer at a mass ratio of 18% relative to the drug-containing particles.

Comparative Example 6

A similar procedure to that for Example 16 was performed, giving drug-containing particles as Comparative Example 6.

Figure 6:
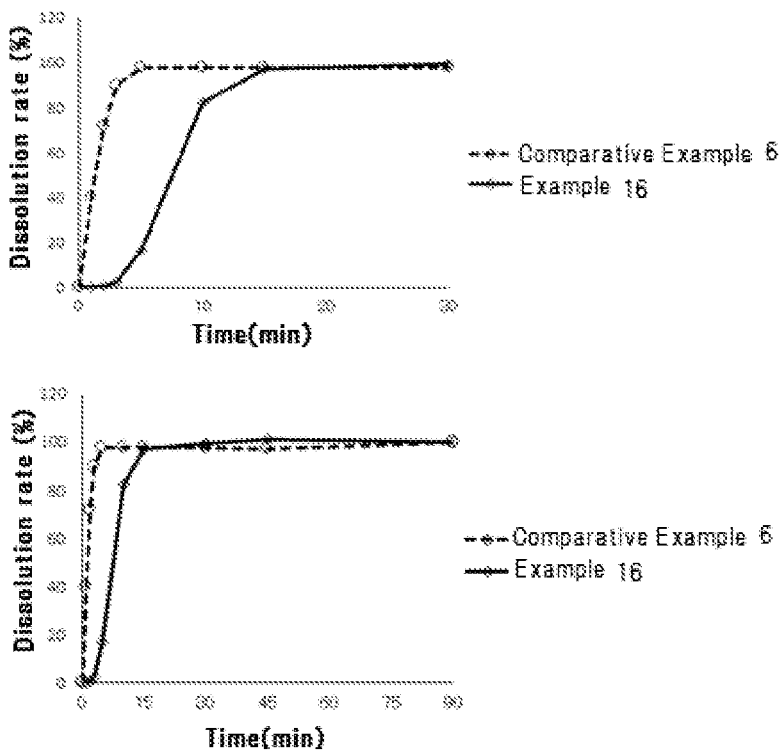
FIG. 6 is graphs showing the drug dissolution test results of masking particles each comprising a core particle containing a drug and an acid, an interlayer containing a carbonate, and a coating layer, and the interlayer contains a binder different from that in the masking particles in FIG. 1.

The masking particles of Example 16 and the drug-containing particles of Comparative Example 6 were subjected to the dissolution test. Changes in dissolution rate of levofloxacin hydrate are shown in FIG. 6. The upper graph in FIG. 6 shows the results for 30 minutes after the start of the test, and the lower graph shows the results for 90 minutes after the start of the test.

In Example 16, polyethylene glycol was used in the interlayer in place of hydroxypropyl cellulose in Example 3. In Example 16, the coating layer containing a water-insoluble polymer prevented water infiltration for a certain period of time, and then water infiltrated. The resulting foaming caused membrane disruption from the inside to rapidly release the drug. As a result, a lag time of 2.1 minutes and a rapid drug release rate of 13.2%/min were satisfied. The results reveal that the drug release suppression for a certain period of time and the subsequent rapid drug release can be achieved, independent of the type of binder.

In contrast, in Comparative Example 6, the drug release was rapid by foaming, but no lag time was observed because the particles lacked the coating layer containing a water-insoluble polymer.

(7) Exchange of Layers Containing Acid and Carbonate

Example 17

[Preparation of Core Particles]

In an agitation mixing granulator, 375 g of levofloxacin hydrate, 225 g of pulverized sodium hydrogen carbonate, and 150 g of low-substituted hydroxypropyl cellulose were placed a mixed, and then 525 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Coating Liquid for Interlayer (5)]

To a solution of 16 g of hydroxypropyl cellulose in 960 g of absolute ethanol, 33.3 g of talc and 60 g of citric acid hydrate were added, and the whole was stirred to give a coating liquid (5).

[Preparation of Drug-Containing Particles]

In a tumbling fluidized-bed coating machine, 200 g of the resulting core particles were placed, and the coating liquid (5) was sprayed to give drug-containing particles coated with 109.3 g of an interlayer.

[Preparation of Masking Particles]

In a tumbling fluidized-bed coating machine, 200 g of the resulting drug-containing particles were placed, and the coating liquid (2) was sprayed to give masking particles. The particles had a masking layer at a mass ratio of 30, relative to the drug-containing particles.

Examples 18 to 20

[Preparation of Masking Particles]

In a tumbling fluidized-bed coating machine, 200 g of the same drug-containing particles as those of Example 17 were placed, and the coating liquid (3) was sprayed to give masking particles. Relative to the mass of the drug-containing particles, particles having a masking layer at a mass ratio of 6% were regarded as Example 18, particles having a masking layer at a mass ratio of 12% were regarded as Example 19, and particles having a masking layer at a mass ratio of 18% were regarded as Example 20.

Comparative Example 7

A similar procedure to that for Examples 17 to 20 was performed, giving drug-containing particles as Comparative Example 7.

Figure 7:
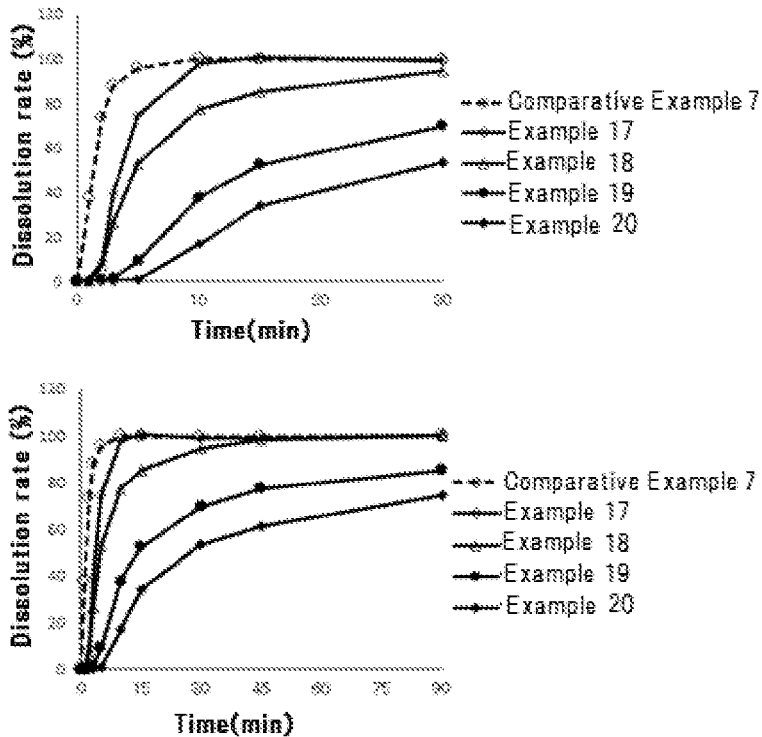
FIG. 7 is graphs showing the drug dissolution test results of masking particles each comprising a core particle containing a drug and a carbonate, an interlayer containing an acid, and a coating layer.

The masking particles of Examples 17 to 20 and the drug-containing particles of Comparative Example 7 were subjected to the dissolution test. Changes in dissolution rate of levofloxacin hydrate are shown in FIG. 7. The upper graph in FIG. 7 shows the results for 30 minutes after the start of the test, and the lower graph shows the results for 90 minutes after the start of the test.

Examples 17 to 20 differ from Examples 1 to 16 in that the core particles contain sodium hydrogen carbonate, and the interlayer contains citric acid hydrate. In Examples 17 to 20, similarly, lag times of 1 to 5.1 minutes and rapid drug release rates of 3.4 to 30.4%/min were satisfied. The results reveal that the drug release suppression for a certain period of time and the subsequent rapid drug release can be achieved even when the portions containing an acid and a carbonate are exchanged.

In contrast, in Comparative Example 7, the drug release was rapid by foaming, but no lag time was observed because the particles lacked the coating layer containing a water-insoluble polymer.

The formulae of the drug-containing particles of Examples 1 to 20 and Comparative Examples 1 to 7 are shown in Table 1.

TABLE 1

(Unit mg)

| | Ingredient | Comparative Example 1 Example 1-7 | Comparative Example 2 Comparative Example 3 | Comparative Example 4 Example 8-11 | Comparative Example 5 Example 12-15 | Comparative Example 6 Example 16 | Comparative Example 7 Example 17-20 |
|---|---|---|---|---|---|---|---|
| Core particle | Levofloxacin hydrate | 256.3 | 256.3 | 256.3 | 256.3 | 256.3 | 256.3 |
| | Citric acid hydrate | 153.8 | — | 59.1 | 17.1 | 153.8 | — |
| | Eythritol | — | 153.8 | — | — | — | — |
| | Sodium hydrogen carbonate | — | — | — | — | — | 153.8 |
| | Low-substituted hydroxypropyl cellulose | 102.5 | 102.5 | 78.9 | 68.3 | 102.5 | 102.5 |
| Interlayer | Hydroxypropyl cellulose | 41 | 41 | 15.8 | 4.6 | — | 41 |
| | Polyethylene glycol | — | — | — | — | 41 | — |
| | Talc | 85.4 | 85.4 | 32.9 | 9.5 | 85.4 | 85.4 |
| | Sodium hydrogen carbonate | 153.8 | 153.8 | 59.1 | 17.1 | 153.8 | — |
| | Citric acid hydrate | — | — | — | — | — | 153.8 |
| | Total | 792.8 | 792.8 | 502.1 | 372.9 | 792.8 | 792.8 |

(8) Content of Disintegrant

Example 21

[Preparation of Core Particles]

In an agitation mixing granulator, 325 g of levofloxacin hydrate, 195 g of pulverized citric acid hydrate, 32.5 g of low-substituted hydroxypropyl cellulose, and 97.5 g of erythritol were placed and mixed, and then 195 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]

In a tumbling fluidized-bed coating machine, 200 g of the resulting core particles were placed, and the coating liquid (1) was sprayed to give drug-containing particles coated with 109.3 g of an interlayer.

[Preparation of Masking Particles]

In a tumbling fluidized-bed coating machine, 200 g of the resulting drug-containing particles were placed, and the coating liquid (2) was sprayed to give masking particles.

The particles had a masking layer at a mass ratio of 18% relative to the mass of the drug-containing particles.

Comparative Example 8

A similar procedure to that for Example 21 was performed, giving drug-containing particles as Comparative Example 8.

Figure 8:
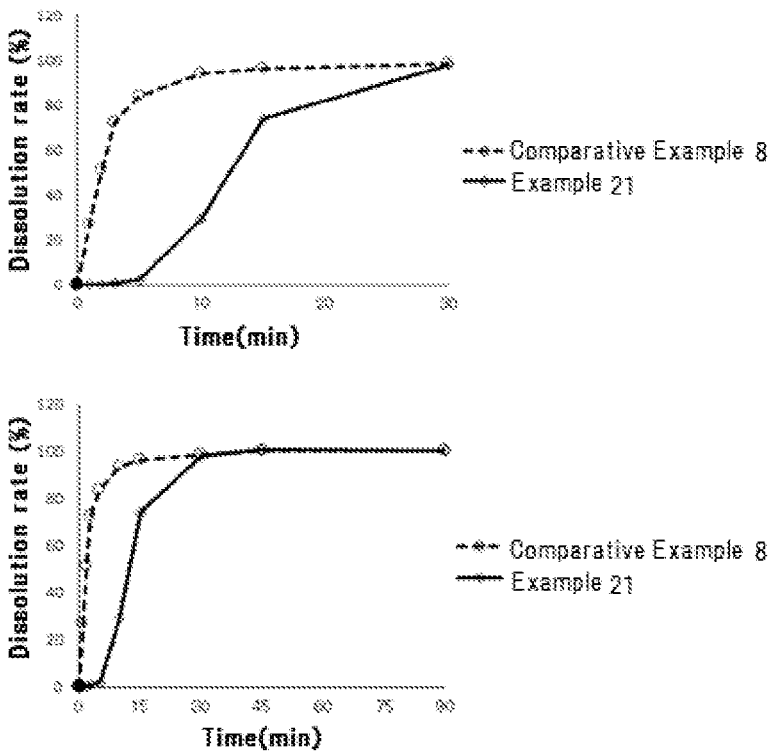
FIG. 8 is graphs showing the drug dissolution test results of masking particles each comprising a core particle containing a drug and an acid, an interlayer containing a carbonate, and a coating layer, and the content of the disintegrant in the core particle differs from that in the masking particles in FIG. 1.

The masking particles of Example 21 and the drug-containing particles of Comparative Example 8 were subjected to the dissolution test. Changes in dissolution rate of levofloxacin hydrate are shown in FIG. 8. The upper graph in FIG. 8 shows the results for 30 minutes after the start of the test, and the lower graph shows the results for 90 minutes after the start of the test.

In the formula of Example 21, the amount of the low-substituted hydroxypropyl cellulose was ¼ that in Example 3, and the corresponding amount of erythritol was added. In Example 21, similarly, a lag time of 3.1 minutes and a rapid drug release rate of 9.0%/min were satisfied. The results reveal that the drug release suppression for a certain period of time and the subsequent rapid drug release can be achieved even when the disintegrant is contained in a small amount.

In contrast, in Comparative Example 8, the drug release was rapid by foaming, but no lag time was observed because the particles lacked the coating layer containing a water-insoluble polymer.

(9) Content Ratio of Acid to Carbonate

Examples 22 to 24

[Preparation of Core Particles]

In an agitation mixing granulator, 400 g of levofloxacin hydrate, 240 g of pulverized citric acid hydrate, and 160 g of low-substituted hydroxypropyl cellulose were placed and mixed, and then 560 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]

In a tumbling fluidized-bed coating machine, 200 g of the resulting core particles were placed, and the coating liquid (1) was sprayed to give drug-containing particles coated with 54.7 g of an interlayer.

[Preparation of Masking Particles]

In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 18% were regarded as Example 22, particles having a masking layer at a mass ratio of 24% were regarded as Example 23, and particles having a masking layer at a mass ratio of 30% were regarded as Example 24.

Comparative Example 9

A similar procedure to that for Examples 22 to 24 was performed, giving drug-containing particles as Comparative Example 9.

Examples 25 to 27

[Preparation of Core Particles]

In an agitation mixing granulator, 400 g of levofloxacin hydrate, 240 g of pulverized citric acid hydrate, and 160 g of low-substituted hydroxypropyl cellulose were placed and mixed, and then 560 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]

In a tumbling fluidized-bed coating machine, 200 g of the resulting core particles were placed, and the coating liquid (1) was sprayed to give drug-containing particles coated with 18.23 g of an interlayer.

[Preparation of Masking Particles]

In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 18% were regarded as Example 25, particles having a masking layer at a mass ratio of 24% were regarded as Example 26, and particles having a masking layer at a mass ratio of 30%, were regarded as Example 27.

Comparative Example 10

A similar procedure to that for Examples 25 to 27 was performed, giving drug-containing particles as Comparative Example 10.

Examples 28 to 30

[Preparation of Core Particles]

In an agitation mixing granulator, 390 g of levofloxacin hydrate, 90 g of pulverized citric acid hydrate, and 180 g of low-substituted hydroxypropyl cellulose were placed and mixed, and then 480 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]

In a tumbling fluidized-bed coating machine, 200 g of the resulting core particles were placed, and the coating liquid (1) was sprayed to give drug-containing particles coated with 109.3 g of an interlayer.

[Preparation of Masking Particles]

In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 125 were regarded as Example 28, particles having a masking layer at a mass ratio of 18% were regarded as Example 29, and particles having a masking layer at a mass ratio of 24% were regarded as Example 30.

Comparative Example 11

A similar procedure to that for Examples 28 to 30 was performed, giving drug-containing particles as Comparative Example 11.

Examples 31 to 33

[Preparation of Core Particles]
In an agitation mixing granulator, 390 g of levofloxacin hydrate, 90 g of pulverized citric acid hydrate, and 180 g of low-substituted hydroxypropyl cellulose were placed and mixed, and then 480 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]
In a tumbling fluidized-bed coating machine, 200 g of the resulting core particles were placed, and the coating liquid (1) was sprayed to give drug-containing particles coated with 18.23 g of an interlayer.

[Preparation of Masking Particles]
In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 18% were regarded as Example 31, particles having a masking layer at a mass ratio of 24% were regarded as Example 32, and particles having a masking layer at a mass ratio of 30% were regarded as Example 33.

Comparative Example 12

A similar procedure to that for Examples 31 to 33 was performed, giving drug-containing particles as Comparative Example 12.

Example 34

[Preparation of Core Particles]
In an agitation mixing granulator, 600 g of levofloxacin hydrate, 40 g of pulverized citric acid hydrate, and 160 g of low-substituted hydroxypropyl cellulose were placed and mixed, and then 560 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]
In a tumbling fluidized-bed coating machine, 200 g of the resulting core particles were placed, and the coating liquid (1) was sprayed to give drug-containing particles coated with 109.3 g of an interlayer.

[Preparation of Masking Particles]
In a tumbling fluidized-bed coating machine, 200 g of the resulting drug-containing particles were placed, and the coating liquid (2) was sprayed to give masking particles.

The particles had a masking layer at a mass ratio of 12% relative to the mass of the drug-containing particles.

Comparative Example 13

A similar procedure to that for Example 34 was performed, giving drug-containing particles as Comparative Example 13.

Examples 35 and 36

[Preparation of Core Particles]
In an agitation mixing granulator, 600 g of levofloxacin hydrate, 40 g of pulverized citric acid hydrate, and 160 g of low-substituted hydroxypropyl cellulose were placed and mixed, and then 560 g of purified water was sprayed while the mixture was stirred, giving a kneaded mixture.

Next, the kneaded mixture was extrusion-granulated by using a wet extrusion granulator, Multigran, and the resulting particles were rounded by using a spherical granulator, Marumerizer. The product was then sieved, and particles passed through a 30-mesh (500 μm) sieve but not passed through a 42-mesh (355 μm) sieve were collected as core particles.

[Preparation of Drug-Containing Particles]
In a tumbling fluidized-bed coating machine, 200 g of the resulting core particles were placed, and the coating liquid (1) was sprayed to give drug-containing particles coated with 54.7 g of an interlayer.

[Preparation of Masking Particles]
In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 125 were regarded as Example 35, and particles having a masking layer at a mass ratio of 18% were regarded as Example 36.

Comparative Example 14

A similar procedure to that for Examples 35 and 36 was performed, giving drug-containing particles as Comparative Example 14.

The masking particles of Examples 22 to 36 and the drug-containing particles of Comparative Examples 9 to 14 were subjected to the dissolution test.

Figure 9:
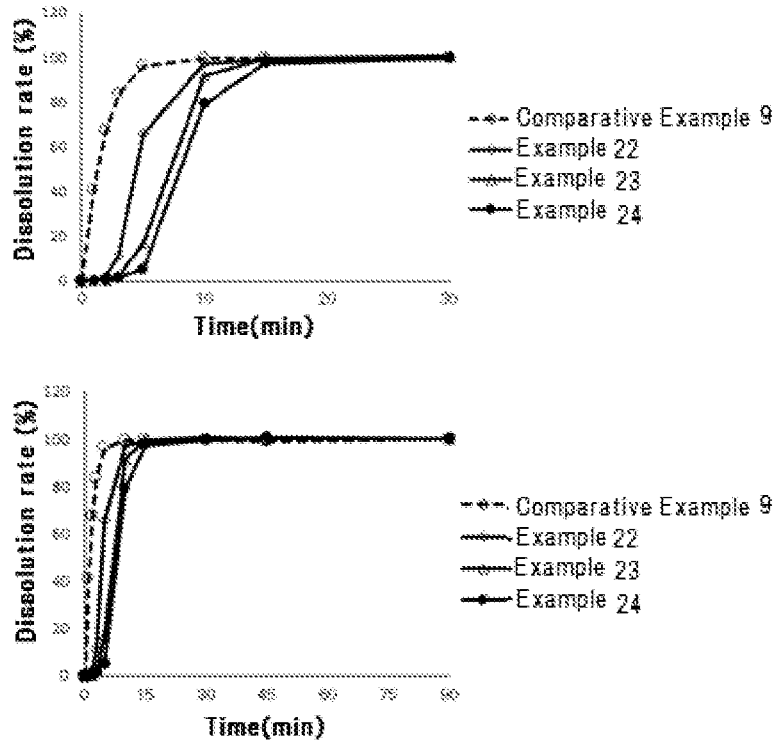
FIG. 9 is graphs showing the drug dissolution test results of masking particles each comprising a core particle containing a drug and an acid, an interlayer containing a carbonate, and a coating layer, and the content ratio of the acid to the carbonate differs from that in the masking particles in FIG. 1.
Figure 10:
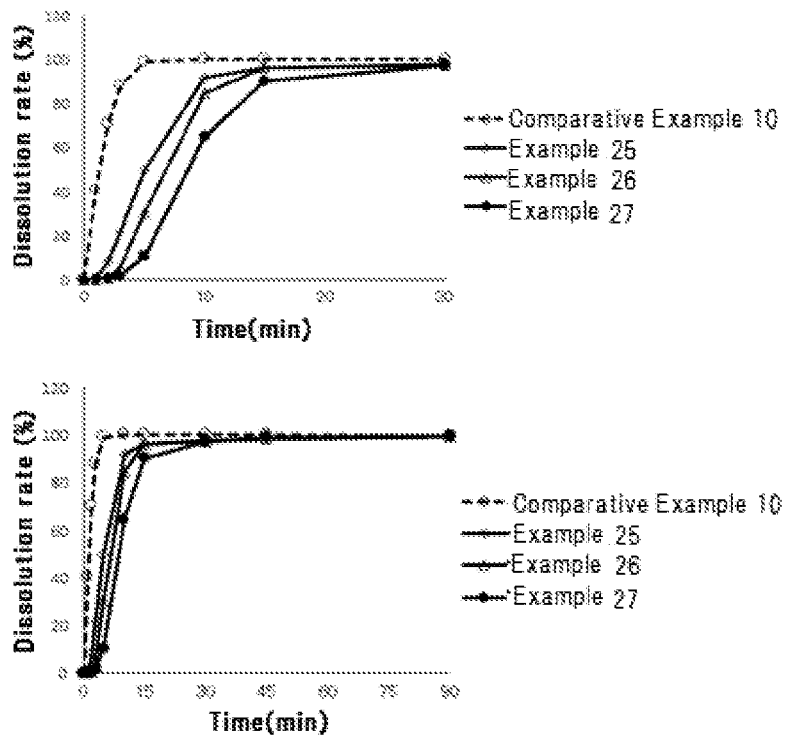
FIG. 10 is graphs showing the drug dissolution test results of masking particles each comprising a core particle containing a drug and an acid, an interlayer containing a carbonate, and a coating layer, and the content ratio of the acid to the carbonate differs from that in the masking particles in FIG. 1.
Figure 11:
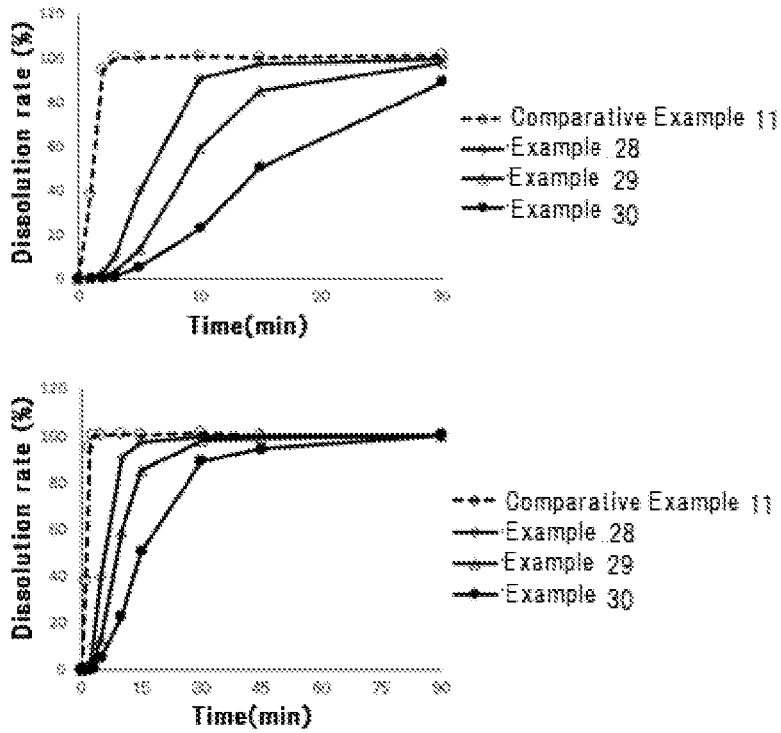
FIG. 11 is graphs showing the drug dissolution test results of masking particles each comprising a core particle containing a drug and an acid, an interlayer containing a carbonate, and a coating layer, and the content ratio of the acid to the carbonate differs from that in the masking particles in FIG. 4.
Figure 12:
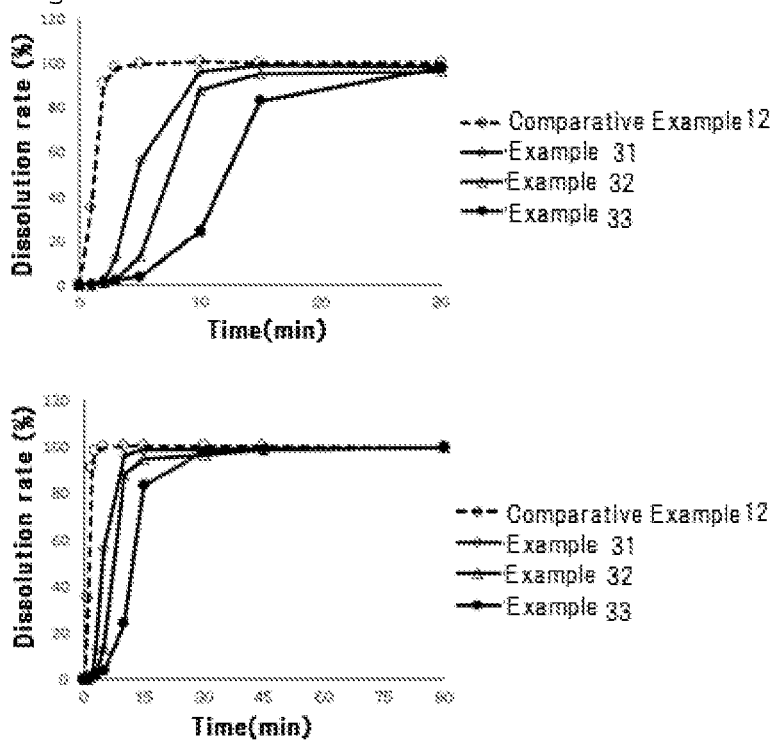
FIG. 12 is graphs showing the drug dissolution test results of masking particles each comprising a core particle containing a drug and an acid, an interlayer containing a carbonate, and a coating layer, and the content ratio of the acid to the carbonate differs from that in the masking particles in FIG. 4.
Figure 13:
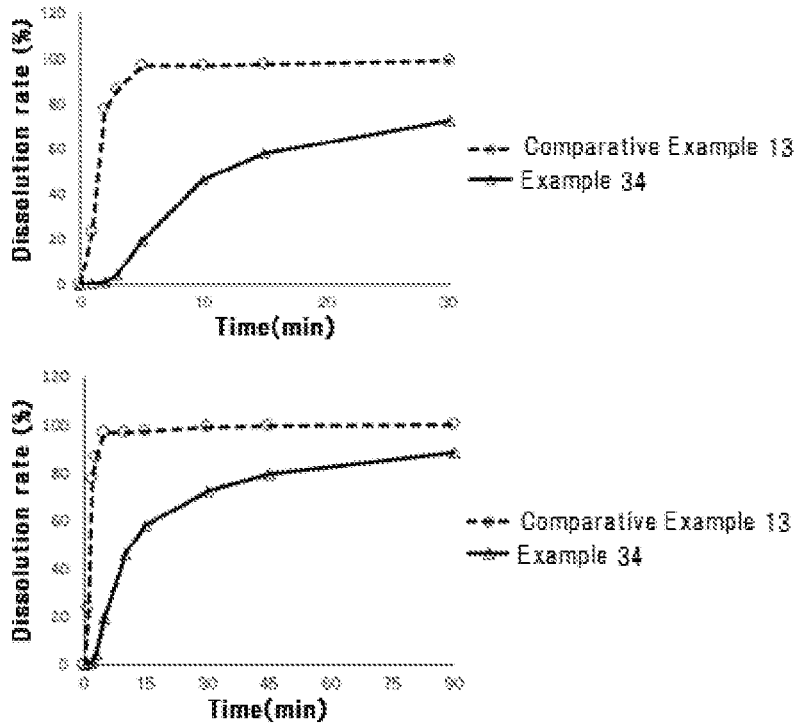
FIG. 13 is graphs showing the drug dissolution test results of masking particles each comprising a core particle containing a drug and an acid, an interlayer containing a carbonate, and a coating layer, and the content ratio of the acid to the carbonate differs from that in the masking particles in FIG. 5.
Figure 14:
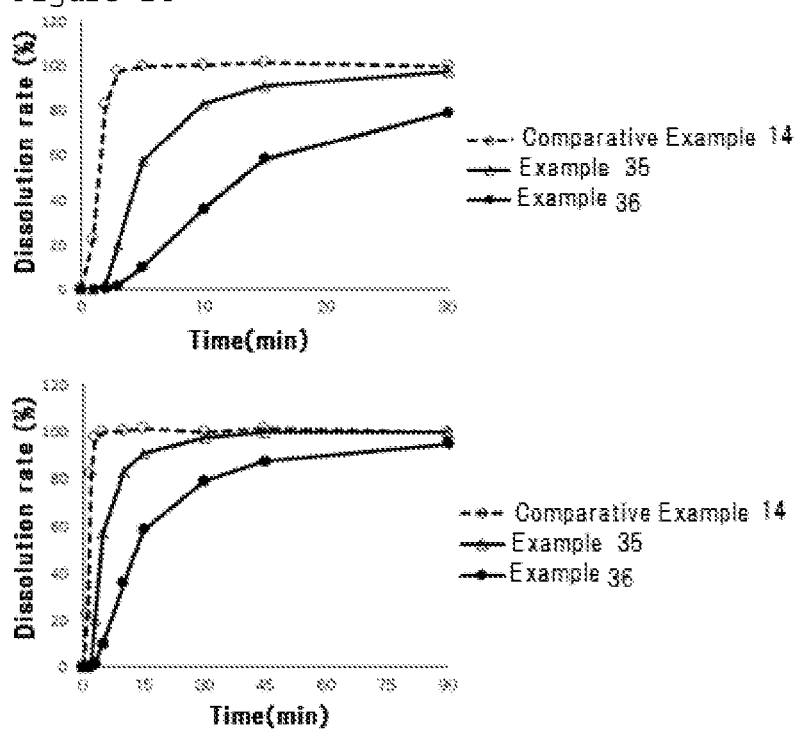
FIG. 14 is graphs showing the drug dissolution test results of masking particles each comprising a core particle containing a drug and an acid, an interlayer containing a carbonate, and a coating layer, and the content ratio of the acid to the carbonate differs from that in the masking particles in FIG. 5.

Changes in dissolution rate of levofloxacin hydrate are shown in FIG. 9 to 14. FIG. 9 shows the results of the masking particles of Examples 22 to 24 and the drug-containing particles of Comparative Example 9, FIG. 10 shows the results of the masking particles of Examples 25 to 27 and the drug-containing particles of Comparative Example 10, FIG. 11 shows the results of the masking particles of Examples 28 to 30 and the drug-containing particles of Comparative Example 11, FIG. 12 shows the results of the masking particles of Examples 31 to 33 and the drug-containing particles of Comparative Example 12, FIG. 13 shows the results of the masking particles of Example 34 and the drug-containing particles of Comparative Example 13, and FIG. 14 shows the results of the masking particles of Examples 35 and 36 and the drug-containing particles of Comparative Example 14. The upper graphs in FIGS. 9 to 14 show the results for 30 minutes after the start of the test, and the lower graphs show the results for 90 minutes after the start of the test.

In Examples 22 to 24, the amount of sodium hydrogen carbonate was one-half that in Examples 3 to 5. In other words, the weight ratio of sodium hydrogen carbonate to 1 part by weight of citric acid hydrate is 1 part by weight in Examples 3 to 5, whereas the weight ratio is 0.5 part by weight in Examples 22 to 24.

In Examples 25 to 27, the amount of sodium hydrogen carbonate was ⅙ that in Examples 3 to 5. In other words, the weight ratio of sodium hydrogen carbonate to 1 part by weight of citric acid hydrate is 1 part by weight in Examples 3 to 5, whereas the weight ratio is 0.17 part by weight in Examples 25 to 27.

14.7%/min were satisfied (FIG. 11). In Examples 31 to 33, lag times of 1.6 to 1.8 minutes and rapid drug release rates of 4.1 to 21.8%/min were satisfied (FIG. 12). In Example 34, a lag time of 2.0 minutes and a rapid drug release rate of 7.5%/min were satisfied (FIG. 13). In Examples 35 and 36, lag times of 1.4 to 2.5 minutes and rapid drug release rates of 5.2 to 18.7%/min were satisfied (FIG. 14).

The drug release suppression time for a certain period of time and the rapid drug release were achieved even when the content of a carbonate was varied in a wide range of 0.17 to 6 parts by weight relative to 1 part by weight of an acid.

In contrast, in Comparative Examples 9 to 14, the drug release was rapid by foaming, but no lag time was observed because the particles lacked the coating layer containing a water-insoluble polymer.

The formulae of the drug-containing particles of Examples 21 to 36 and Comparative Examples 8 to 14 are shown in Table 2.

TABLE 2

(Unit mg)

| | Ingredient | Comparative Example 3 Example 21 | Comparative Example 9 Example 22-24 | Comparative Example 10 Example 25-27 | Comparative Example 11 Example 28-30 | Comparative Example 12 Example 31-33 | Comparative Example 13 Example 34 | Comparative Example 14 Example 35-36 |
|---|---|---|---|---|---|---|---|---|
| Core particle | Levofloxacin hydrate | 256.3 | 256.3 | 256.3 | 256.3 | 256.3 | 256.3 | 256.3 |
| | Citric acid hydrate | 153.8 | 153.8 | 153.8 | 59.1 | 59.1 | 17.1 | 17.1 |
| | Erythritol | 76.9 | — | — | — | — | — | — |
| | Low-substituted hydroxypropyl cellulose | 25.6 | 102.5 | 102.5 | 78.9 | 78.9 | 68.3 | 68.3 |
| Interlayer | Hydroxypropyl cellulose | 41 | 20.5 | 6.8 | 31.5 | 5.3 | 27.3 | 13.7 |
| | Talc | 85.4 | 42.7 | 14.2 | 65.7 | 11 | 57 | 28.5 |
| | Sodium hydrogen carbonate | 153.8 | 76.9 | 25.6 | 118.3 | 19.7 | 102.5 | 51.3 |
| | Total | 792.8 | 652.7 | 559.2 | 609.8 | 430.3 | 528.5 | 435.2 |

In Examples 28 to 30, the amount of sodium hydrogen carbonate was double that in Examples 9 to 11. In other words, the weight ratio of sodium hydrogen carbonate to 1 part by weight of citric acid hydrate is 1 part by weight in Examples 9 to 11, whereas the weight ratio is 2 parts by weight in Examples 28 to 30.

In Examples 31 to 33, the amount of sodium hydrogen carbonate was ⅓ that in Examples 9 to 11. In other words, the weight ratio of sodium hydrogen carbonate to 1 part by weight of citric acid hydrate is 1 part by weight in Examples 9 to 11, whereas the weight ratio is 0.33 part by weight in Examples 31 to 33.

In Example 34, the amount of sodium hydrogen carbonate was six times that in Example 12. In other words, the weight ratio of sodium hydrogen carbonate to 1 part by weight of citric acid hydrate is 1 part by weight in Example 12, whereas the weight ratio is 6 parts by weight in Example 34.

In Examples 35 and 36, the amount of sodium hydrogen carbonate was three times that in Examples 12 and 13. In other words, the weight ratio of sodium hydrogen carbonate to 1 part by weight of citric acid hydrate is 1 part by weight in Examples 12 and 13, whereas the weight ratio is 3 parts by weight in Examples 35 and 36.

In Examples 22 to 24, lag times of 1.3 to 2.6 minutes and rapid drug release rates of 14.8 to 27.3%/min were satisfied (FIG. 9). In Examples 25 to 27, lag times of 1.1 to 2.2 minutes and rapid drug release rates of 10.8 to 13.3%/min were satisfied (FIG. 10). In Examples 28 to 30, lag times of 1.3 to 3.1 minutes and rapid drug release rates of 3.5 to

(10) Structure of Drug-Containing Particles
Drug-Containing Particles Each Comprising a Core Particle and Two Interlayers Examples 37 to 39

[Preparation of Coating Liquid (6)]

To 857 g of absolute ethanol, 60 g of citric acid hydrate was added, and the whole was stirred to give a coating liquid (6).

[Preparation of Interlayer I-Coated Particles]

In a tumbling fluidized-bed coating machine, 200 g of the core particles of Comparative Example 2 were placed, and the coating liquid (6) was sprayed to give interlayer I-coated particles coated with 60 g of an interlayer I.

[Preparation of Drug-Containing Particles]

In a tumbling fluidized-bed coating machine, 200 g of the resulting interlayer I-coated particles were placed, and the coating liquid (1) was sprayed to give drug-containing particles coated with 84.1 g of an interlayer II.

[Preparation of Masking Particles]

In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 30% were regarded as Example 37, particles having a masking layer at a mass ratio of 361 were regarded as Example 38, and particles having a masking layer at a mass ratio of 42% were regarded as Example 39.

Comparative Example 15

A similar procedure to that for Examples 37 to 39 was performed, giving drug-containing particles as Comparative Example 15.

The masking particles of Examples 37 to 39 and the drug-containing particles of Comparative Example 15 were subjected to the dissolution test.

Figure 15:
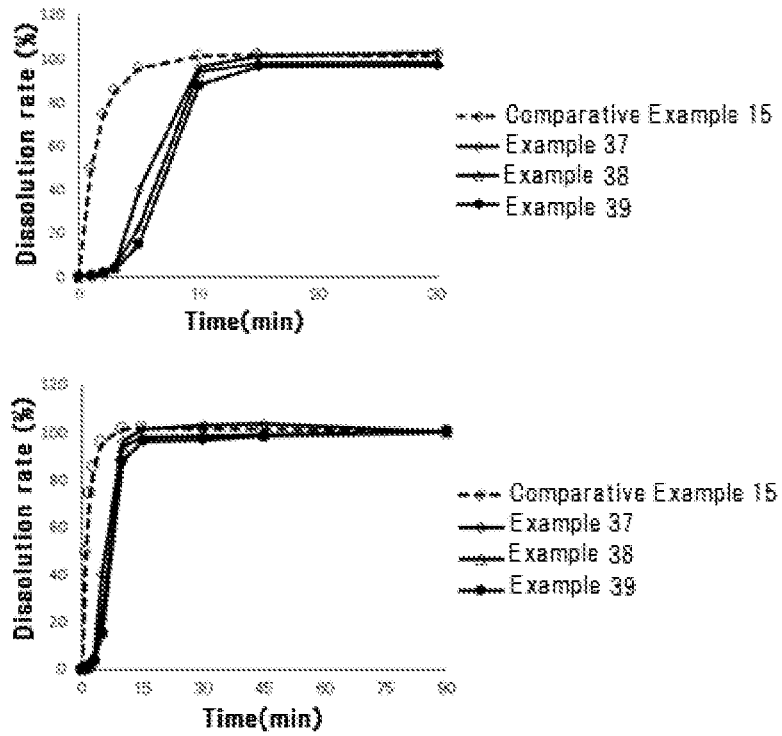
FIG. 15 is graphs showing the drug dissolution test results of masking particles each comprising a core particle containing a drug, a first interlayer containing an acid, a second interlayer containing a carbonate, and a coating layer.

Changes in dissolution rate of levofloxacin hydrate are shown in FIG. 15. The upper graph in FIG. 15 shows the results for 30 minutes after the start of the test, and the lower graph shows the results for 90 minutes after the start of the test.

In Examples 37 to 39, core particles containing a drug were coated with an interlayer I containing citric acid hydrate, and the coated particles were coated with an interlayer containing a sodium hydrogen carbonate to give drug-containing particles, which were further coated with a coating layer containing a water-insoluble polymer. In Examples 37 to 39, similarly, lag times of 1.3 to 2.2 minutes and rapid drug release rates of 6.0 to 17.5%/min were satisfied.

The drug release suppression time and the drug release rate were appropriately controllable even when drug-containing particles separately containing a drug, an acid, and a carbonate were used. The masking particles having the above structure can be suitably used for a drug unstable to acid or alkali.

Relative to the drug-containing particles, the particles had the coating layer at a content ratio of 30 to 42% by weight, which was more than 6 to 30% by weight in Examples 1 to 36, but an appropriate lag time and drug release rate were achieved.

Drug-Containing Particles Each Comprising a Core Particle Coated with a Drug and Three Interlayers Examples 40 to 42

[Preparation of Core Particles]
Of 1,000 g of spherical granules of D-mannitol (Freund Corporation; NONPAREIL 108 (100), hereinafter the same applies), granules passed through a 100-mesh (150 μm) sieve but not passed through a 200-mesh (75 μm) sieve were collected as core particles.
[Preparation of Coating Liquid (7)]
To a mixed liquid of 158 g of purified water and 68 g of absolute ethanol, hypromellose (manufactured by Shin-Etsu Chemical; TC-5R, hereinafter the same applies) was added and dissolved. Then, 45 g of levofloxacin hydrate was added, and the whole was stirred to give a coating liquid (7).
[Preparation of Drug Layer-Coated Particles]
In a tumbling fluidized-bed coating machine, 593.7 g of the above core particles were placed, and the coating liquid (7) was sprayed to give drug layer-coated particles coated with 56.3 g of a drug layer.
[Preparation of Coating Liquid (8)]
To 276 g of purified water, 45 g of D-mannitol (ROQUETTE; PEALITOL50C, hereinafter the same applies) was added, and the whole was stirred to give a coating liquid (8).
[Preparation of Interlayer I-Coated Particles]
In a tumbling fluidized-bed coating machine, 150 g of the above drug layer-coated particles were placed, and the coating liquid (8) was sprayed to give interlayer I-coated particles coated with 45 g of an interlayer I.
[Preparation of Coating Liquid (9)]
To a mixed liquid of 420 g of purified water and 180 g of absolute ethanol, 60 g of citric acid hydrate and 30 g of D-mannitol were added, and the whole was stirred to give a coating liquid (9).
[Preparation of Interlayer II-Coated Particle]
In a tumbling fluidized-bed coating machine, 125 g of the above interlayer I-coated particles were placed, and the coating liquid (9) was sprayed to give interlayer II-coated particles coated with 43.3 g of an interlayer II.
[Preparation of Drug-Containing Particles]
In a tumbling fluidized-bed coating machine, 125 g of the resulting interlayer II-coated particles were placed, and the coating liquid (1) was sprayed to give drug-containing particles coated with 117.2 g of an interlayer III.
[Preparation of Masking Particles]
In a tumbling fluidized-bed coating machine, 200 g of the resulting drug-containing particles were placed, and the coating liquid (2) was sprayed to give masking particles.

Relative to the mass of the drug-containing particles, particles having a masking layer at a mass ratio of 54% were regarded as Example 40, particles having a masking layer at a mass ratio of 66 were regarded as Example 41, and particles having a masking layer at a mass ratio of 78% were regarded as Example 42.

Comparative Example 16

A similar procedure to that for Examples 40 to 42 was performed, giving drug-containing particles as Comparative Example 16.

Figure 16:
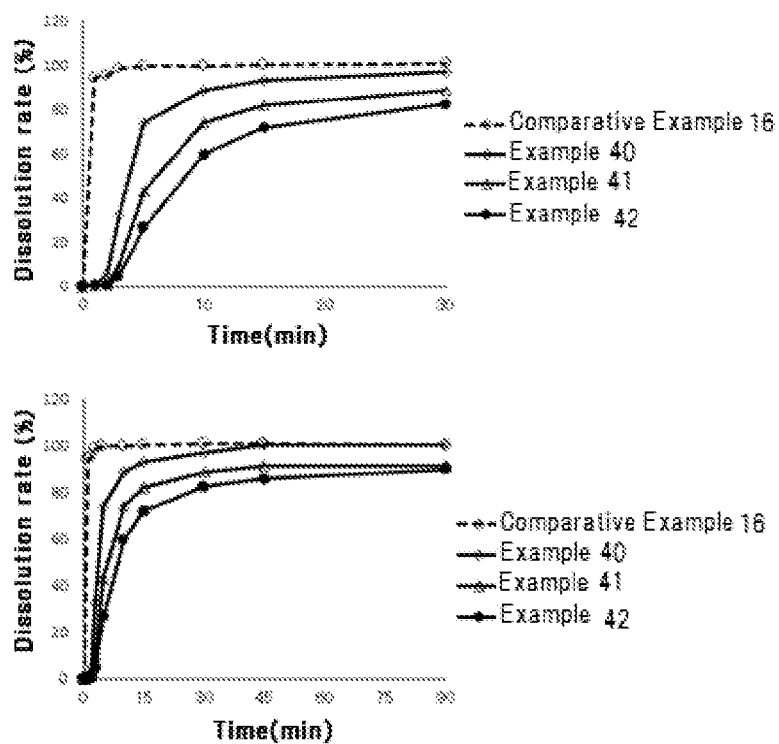
FIG. 16 is graphs showing the drug dissolution test results of masking particles each comprising a core particle coated with a drug, a first interlayer consisting of a diluent, a second interlayer containing an acid, a third interlayer containing a carbonate, and a coating layer.

The masking particles of Examples 40 to 42 and the drug-containing particles of Comparative Example 16 were subjected to the dissolution test. Changes in dissolution rate of levofloxacin hydrate are shown in FIG. 16. The upper graph in FIG. 16 shows the results for 30 minutes after the start of the test, and the lower graph shows the results for 90 minutes after the start of the test.

In Examples 40 to 42, diluent core particles with a coating containing a drug were coated with an interlayer I of a diluent, and the coated particles were further coated with an interlayer II containing citric acid hydrate. The resulting particles were coated with an interlayer III containing sodium hydrogen carbonate to give drug-containing particles, which were further coated with a coating layer containing a water-insoluble polymer. In Examples 40 to 42, similarly, lag times of 1.0 to 2.0 minutes and rapid drug release rates of 10.9 to 27.2%/min were satisfied.

By providing an interlayer between the drug-containing layer and the acid-containing layer or the carbonate-containing layer, the drug release suppression time and the drug release rate were appropriately controllable even when drug-containing particles in which the drug was in contact with neither the acid nor the carbonate were used. The masking particles having the above structure can be suitably used for a drug extremely unstable to acid or alkali.

Relative to the drug-containing particles, the particles had the coating layer at a content ratio of 54 to 78% by weight, which was extremely more than 6 to 30% by weight in Examples 1 to 36, but an appropriate lag time and drug release rate were achieved.

The masking particles of Examples 40 to 42 comprise smaller core particles than those in Examples 1 to 39, and accordingly the masking particles are fine. The technique can be used to appropriately control the drug release suppression time and the drug release rate, independent of the particle size of masking particles.

The formula of the drug-containing particles of Examples 37 to 39 and Comparative Example 15 is shown in Table 3, and the formula of the drug-containing particles of Examples 40 to 42 and Comparative Example 16 is shown in Table 4.

TABLE 3

(Unit: mg)

|  | Ingredient | Comparative Example 15 Example 37-39 |
|---|---|---|
| Core particle | Levofloxacin hydrate | 256.3 |
|  | Erythritol | 153.8 |
|  | Low-substituted hydroxypropyl cellulose | 102.5 |
| Interlayer I | Citric acid hydrate | 153.8 |
| Interlayer II | Hydroxypropyl cellulose | 41 |
|  | Talc | 85.4 |
|  | Sodium hydrogen carbonate | 153.8 |
| Total |  | 946.6 |

TABLE 4

(Unit: mg)

|  | Ingredient | Comparative Example 16 Example 40-42 |
|---|---|---|
| Core particle | Spherical granules of D-mannitol | 338.0 |
| Drug layer | Levofloxacin hydrate | 25.6 |
|  | Hypromellose | 6.4 |
| Interlayer I | D-mannitol | 111.0 |
| Interlayer II | Citric acid hydrate | 111.0 |
|  | D-mannitol | 55.5 |
| Interlayer III | Hydroxypropyl cellulose | 88.8 |
|  | Talc | 185.4 |
|  | Sodium hydrogen carbonate | 333.1 |
| Total |  | 1254. |

The above results reveal that masking particles in which drug-containing particles containing a drug, an acid, and a carbonate are coated with a coating layer containing a water-insoluble polymer achieve an appropriate lag time and a rapid drug release rate independent of the structure of drug-containing particles.

(11) Production of Orally Disintegrating Tablets Using Masking Particles

Example 43

[Preparation of Rapidly Disintegrating Granules]

In a fluidized-bed granulator, 374.5 g of D-mannitol, 10.5 g of ethyl cellulose, and 5.3 g of light anhydrous silicic acid were placed and were granulated with a granulation liquid in which 105.5 g of corn starch and 31.6 g of crospovidone were dispersed in 453.6 g of purified water, giving rapidly disintegrating granules.

[Preparation of Tablets]

To a mixture of 935.6 mg of the masking particles of Example 3 and 916.79 mg of the above rapidly disintegrating particles, 18.71 mg of magnesium stearate was added and mixed, and the mixture was placed in a single punch tableting machine (Ichihashi Seiki; HANDTAB-200) and was tableted by using a 16-mm punch, giving tablets having a tablet thickness of 10.5 mm.

Figure 17:
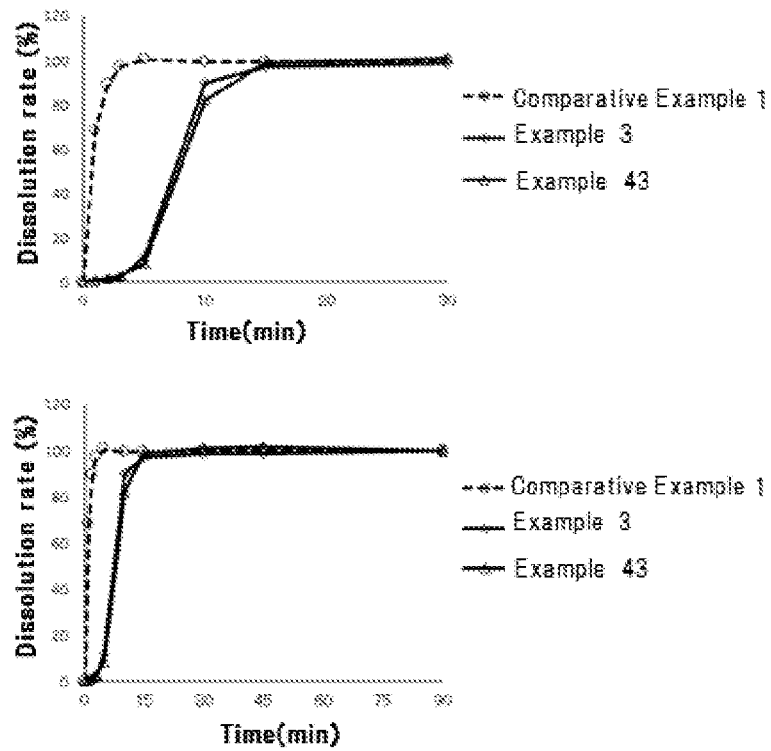
FIG. 17 is graphs showing the drug dissolution test results of masking particles each comprising a core particle containing a drug and an acid, an interlayer containing a carbonate, and a coating layer and of orally disintegrating tablets produced by using the masking particles.

The orally disintegrating tablets of Example 43, the masking particles of Example 3 (particles prepared by coating the drug-containing particles of Comparative Example 1 with 18% by weight of the masking layer), and the drug-containing particles of Comparative Example 1 were subjected to the dissolution test. Changes in dissolution rate of levofloxacin hydrate are shown in FIG. 17. The upper graph in FIG. 17 shows the results for 30 minutes after the start of the test, and the lower graph shows the results for 90 minutes after the start of the test.

The tablets of Example 43 showed substantially the same elution profile as that of the masking particles of Example 3. The results reveal that the masking particles of the present invention can be used to produce tablets, and the resulting tablets suppress the drug release in the mouth and subsequently, rapidly release the drug.

The formula of the orally disintegrating tablets of Example 43 is shown in Table 5.

TABLE 5

(Unit: mg)

|  |  |  | Example 43 |
|---|---|---|---|
| Tablet | Masking particle | Drug-containing particle of Comparative Example 1 | 792.8 |
|  |  | Aminoalkyl methacrylate copolymer E | 71.4 |
|  |  | Talc | 71.4 |
|  |  | Subtotal | 935.6 |
|  | Excipients mixture | Rapidly disintegrating granule | 916.79 |
|  |  | Magnesium stearate | 18.71 |
|  | Total |  | 1871.1 |

(12) Type of Acid and Type of Drug

Example 44

[Preparation of Core Particles]

Of 1,000 g of spherical granules of D-mannitol, granules passed through a 100-mesh (150 μm) sieve but not passed through a 200-mesh (75 μm) sieve were collected as core particles.

[Preparation of Drug Layer-Coated Particles]

In a tumbling fluidized-bed coating machine, 593.7 g of the above core particles were placed, and the coating liquid (7) was sprayed to give drug layer-coated particles coated with 56.3 g of a drug layer.

[Preparation of Interlayer I-Coated Particles]

In a tumbling fluidized-bed coating machine, 150 g of the above drug layer-coated particles were placed, and the coating liquid (8) was sprayed to give interlayer I-coated particles coated with 45 g of an interlayer I.

[Preparation of Coating Liquid (10)]

To a mixed liquid of 420 g of purified water and 180 g of absolute ethanol, 60 g of succinic acid (Wako Pure Chemical Industries) and 30 g of D-mannitol were added, and the whole was stirred to give a coating liquid (10).

[Preparation of Interlayer II-Coated Particles]

In a tumbling fluidized-bed coating machine, 125 g of the above interlayer I-coated particles were placed, and the coating liquid (10) was sprayed to give interlayer II-coated particles coated with 43.3 g of an interlayer II.
[Preparation of Drug-Containing Particles]
In a tumbling fluidized-bed coating machine, 125 g of the above interlayer II-coated particles were placed, and the coating liquid (1) was sprayed to give drug-containing particles coated with 117.2 g of an interlayer III.
[Preparation of Coating Liquid (11)]
In a mixed liquid of 210 g of ethanol and 90 g of purified water, 30 g of aminoalkyl methacrylate copolymers E was dissolved, and 30 g of talc was added. The whole was stirred to give a coating liquid (11).
[Preparation of Masking Particles]
In a tumbling fluidized-bed coating machine, 200 g of the resulting drug-containing particles were placed, and the coating liquid (11) was sprayed to give masking particles.
The particles had a masking layer at a mass ratio of 54% relative to the mass of the drug-containing particles.

Comparative Example 17

Figure 18:
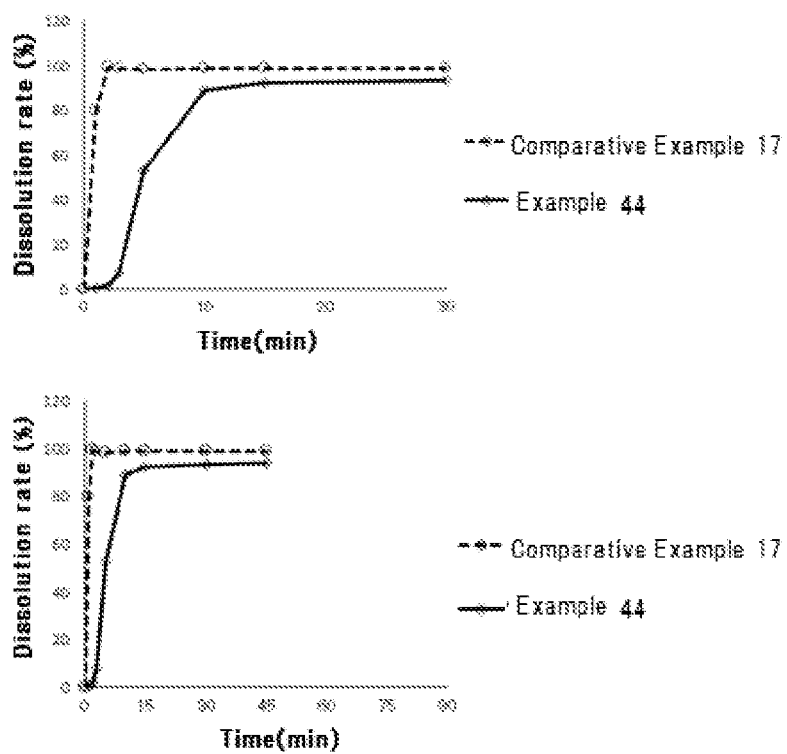
FIG. 18 is graphs showing the drug dissolution test results of masking particles each comprising a core particle coated with a drug, a first interlayer consisting of a diluent, a second interlayer containing an acid, a third interlayer containing a carbonate, and a coating layer, and the acid differs from that in the masking particles in FIG. 16.

A similar procedure to that for Example 44 was performed, giving drug-containing particles as Comparative Example 17.
The masking particles of Example 44 and the drug-containing particles of Comparative Example 17 were subjected to the dissolution test. Changes in dissolution rate of levofloxacin hydrate are shown in FIG. 18. The upper graph in FIG. 18 shows the results for 30 minutes after the start of the test, and the lower graph shows the results for 90 minutes after the start of the test.
In Example 44, core particles containing no drug were coated with a drug layer, and the coated particles were further coated with an interlayer I of a diluent. The resulting particles were coated with an interlayer II containing an acid, and the coated particles were further coated with an interlayer III containing a carbonate. In Example 44, a lag time of 1.1 minutes and a rapid drug release rate of 22.7%/min were satisfied. In contrast, in Comparative Example 17, no lag time was observed because the particles lacked the coating layer containing a water-soluble polymer.
In the masking particles of Example 44, succinic acid was used in the masking particles in place of citric acid in Example 42. Succinic acid having pKas of 4.2 and 5.6 is a weaker acid than citric acid having pKas of 3.1, 4.8, and 6.4, but achieved substantially the same effect. Hence, the acid in the technique may be any acid that is a stronger acid than carbonic acid.
In the masking particles of Example 44, the drug is in direct contact with neither the acid nor the carbonate, and thus such masking particles are further useful for a drug unstable to acid or alkali.
The masking particles of Example 44 comprise smaller core particles than those in Examples 1 to 39, and accordingly the masking particles are fine. The technique can be used to appropriately control the drug release suppression time and the drug release rate, independent of the particle size of masking particles.

Example 45

[Preparation of Core Particles]
Of 1,000 g of spherical granules of D-mannitol, granules passed through a 100-mesh (150 μm) sieve but not passed through a 200-mesh (75 μm) sieve were collected as core particles.

[Preparation of Coating Liquid (12)]
To a mixed liquid of 770 g of purified water and 330 g of absolute ethanol, hypromellose was added and dissolved, and then 220 g of zolpidem tartrate was added. The whole was stirred to give a coating liquid (12).
[Preparation of Drug Layer-Coated Particles]
In a tumbling fluidized-bed coating machine, 358 g of the above core particles were placed, and the coating liquid (12) was sprayed to give drug layer-coated particles coated with 275 g of a drug layer.
[Preparation of Coating Liquid (13)]
To 307 g of purified water, 15.36 g of D-mannitol and 30.72 g of pulverized tartaric acid (manufactured by Kozakai Pharmaceutical, hereinafter the same applies) were added, and the whole was stirred to give a coating liquid (13).
[Preparation of Interlayer I-Coated Particles]
In a tumbling fluidized-bed coating machine, 184.3 g of the above drug layer-coated particles were placed, and the coating liquid (13) was sprayed to give interlayer I-coated particles coated with 46.08 g of an interlayer I.
[Preparation of Coating Liquid (14)]
To 338 g of purified water, 54 g of D-mannitol was added, and the whole was stirred to give a coating liquid (14).
[Preparation of Interlayer II-Coated Particles]
In a tumbling fluidized-bed coating machine, 180 g of the above interlayer I-coated particles were placed, and the coating liquid (14) was sprayed to give interlayer II-coated particles coated with 54 g of an interlayer II.
[Preparation of Coating Liquid (15)]
To a solution of 6.7 g of HPCL in 135 g of absolute ethanol, 13.5 g of talc (manufactured by Nippon Talc; MICRO ACE) and 24.8 g of pulverized sodium hydrogen carbonate were added, and the whole was stirred to give a coating liquid (15).
[Preparation of Drug-Containing Particles]
In a tumbling fluidized-bed coating machine, 210 g of the above interlayer II-coated particles were placed, and the coating liquid (15) was sprayed to give drug-containing particles coated with 45 g of an interlayer III.
[Preparation of Coating Liquid (16)]
In a mixed liquid of 644 g of ethanol and 276 g of purified water, 92 g of aminoalkyl methacrylate copolymer E was dissolved, and 0.92 g of yellow ferric oxide (manufactured by Kishi Kasei) and 276 g of talc (manufactured by Nippon Talc; MICRO ACE) were added. The whole was stirred to give a coating liquid (16).
[Preparation of Masking Particles]
In a tumbling fluidized-bed coating machine, 227.2 g of the resulting drug-containing particles were placed, and the coating liquid (16) was sprayed to give masking particles. The masking particles were sieved, and particles passed through a 60-mesh (250 μm) sieve and not passed through an 83-mesh (180 μm) sieve were collected.
The particles had a masking layer at a mass ratio of 90% relative to the mass of the drug-containing particles.

Comparative Example 18

Figure 19:
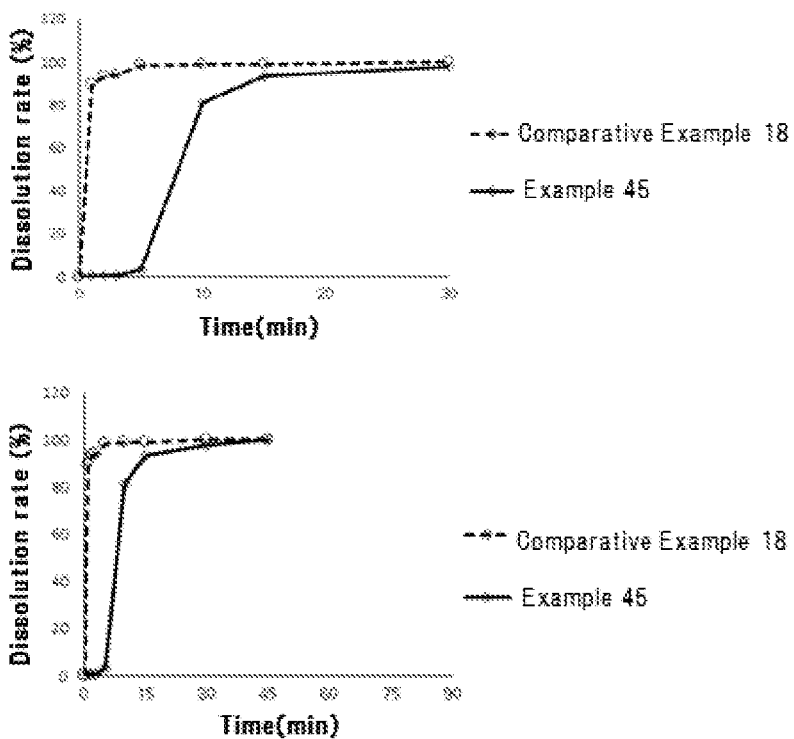
FIG. 19 is graphs showing drug dissolution test results of masking particles each comprising a core particle coated with a drug, a first interlayer containing an acid, a second interlayer consisting of a diluent, a third interlayer containing a carbonate, and a coating layer.

A similar procedure to that for Example 45 was performed, giving drug-containing particles as Comparative Example 18.
The masking particles of Example 45 and the drug-containing particles of Comparative Example 18 were subjected to the dissolution test. Changes in dissolution rate of zolpidem tartrate are shown in FIG. 19. The upper graph in FIG. 19 shows the results for 30 minutes after the start of the test, and the lower graph shows the results for 90 minutes after the start of the test.

In Example 45, core particles containing no drug were coated with a drug layer, and the coated particles were further coated with an interlayer I containing an acid. The resulting particles were coated with an interlayer II of a diluent, and the coated particles were further coated with an interlayer III containing a carbonate. In Example 45, a lag time of 3 minutes and a rapid drug release rate of 12.6%/min were satisfied. In contrast, Comparative Example 18, no lag time was observed because the particles lacked the coating layer containing a water-soluble polymer.

The masking particles of Example 45 differ from Examples 1 to 44 in containing zolpidem tartrate as the drug. The results reveal that the drug release suppression time and the drug release rate can be appropriately controlled independent of the type of drug.

The masking particles of Example 45 also differ from Examples 1 to 44 in containing tartaric acid as the acid. The results reveal that the drug release suppression time and the drug release rate can be appropriately controlled independent of the type of acid.

The masking particles of Example 45 had a masking layer at a mass ratio of 90% relative to the mass of the drug-containing particles, and these particles having a very thick masking layer were also able to appropriately control the drug release suppression time and the drug release rate.

The formula of the drug-containing particles of Example 44 and Comparative Example 17 is shown in Table 6, and the formula of the drug-containing particles of Example 45 and Comparative Example 18 is shown in Table 7.

TABLE 6

(Unit: mg)

| | Ingredient | Comparative Example 17 Example 44 |
|---|---|---|
| Core particle | Spherical granules of D-mannitol | 338.0 |
| Drug layer | Levofloxacin hydrate | 25.6 |
| | Hypromellose | 6.4 |
| Interlayer I | D-mannitol | 111.0 |
| Interlayer II | Succinic acid | 111.0 |
| | D-mannitol | 55.5 |
| Interlayer III | Hydroxypropyl cellulose | 88.8 |
| | Talc | 185.4 |
| | Sodium hydrogen carbonate | 333.1 |
| Total | | 1254. |

TABLE 7

(Unit: mg)

| | Ingredient | Comparative Example 18 Example 45 |
|---|---|---|
| Core particle | Spherical granules of D-mannitol | 16.3 |
| Drug layer | Zolpidem tartrate | 10.0 |
| | Hypromellose | 2.5 |
| Interlayer I | D-mannitol | 2.4 |
| | Tartaric acid | 4.8 |

TABLE 7-continued (Unit: mg)

| | Ingredient | Comparative Example 18 Example 45 |
|---|---|---|
| Interlayer II | D-mannitol | 10.8 |
| Interlayer III | Hydroxypropyl cellulose | 1.5 |
| | Talc | 3.0 |
| | Sodium hydrogen carbonate | 5.5 |
| Total | | 56.8 |

(13) Measurement of Particle Size Distribution

The results of particle size distribution measurement of the masking particles of Examples 1 to 42, 44, and 45 and the core particles, the interlayer-coated particles, and the drug layer-coated particles of Comparative Examples 1 to 18 are shown in Tables 8 to 10.

TABLE 8

(Unit: μm)

| | | $D_{10}$ | $D_{50}$ | $D_{90}$ |
|---|---|---|---|---|
| Comparative Example 1 | Core particle | 374 | 583 | 956 |
| Example 1 | Inter layer-coated particle | 402 | 569 | 830 |
| Example 1 | Masking particle(6%) | 408 | 571 | 817 |
| Example 2 | Masking particle (12%) | 415 | 581 | 830 |
| Example 3 | Masking particle (18%) | 424 | 595 | 847 |
| Example 4 | Masking particle (24%) | 440 | 622 | 901 |
| Example 5 | Masking particle (30%) | 451 | 635 | 921 |
| Comparative Example 2 | Core particle | 394 | 483 | 591 |
| Example 2 | Interlayer-coated particle | 403 | 494 | 617 |
| Comparative Example 3 | Masking particle (18%) | 441 | 534 | 647 |
| Example 6 | Masking particle (9%) | 429 | 686 | 1148 |
| Example 7 | Masking particle (12%) | 425 | 643 | 996 |
| Comparative Example 4 | Core particle | 361 | 543 | 835 |
| Example 4 | Interlayer-coated particle | 381 | 584 | 922 |
| Example 8 | Masking particle (12%) | 388 | 591 | 930 |
| Example 9 | Masking particle (18%) | 400 | 618 | 1004 |
| Example 10 | Masking particle (24%) | 403 | 611 | 965 |
| Example 11 | Masking particle (30%) | 411 | 630 | 1054 |
| Comparative Example 5 | Core particle | 361 | 577 | 1019 |
| Example 5 | Interlayer-coated particle | 366 | 595 | 1170 |
| Example 12 | Masking particle (12%) | 380 | 569 | 866 |
| Example 13 | Masking particle (18%) | 375 | 580 | 973 |
| Example 14 | Masking particle (24%) | 386 | 571 | 859 |
| Example 15 | Masking particle (30%) | 389 | 592 | 978 |
| Comparative Example 6 | Interlayer-coated particle | 415 | 624 | 969 |
| Example 16 | Masking particle (18%) | 426 | 613 | 909 |
| Comparative Example 7 | Core particle | 354 | 453 | 582 |
| Example 7 | Interlayer-coated particle | 361 | 475 | 628 |
| Example 17 | Masking particle (30%) | 407 | 556 | 773 |
| Example 18 | Masking particle (6%) | 409 | 499 | 615 |
| Example 19 | Masking particle (12%) | 410 | 511 | 641 |
| Example 20 | Masking particle (18%) | 410 | 521 | 661 |
| Comparative Example 8 | Core particle | 380 | 605 | 1034 |
| Example 8 | Interlayer-coated particle | 453 | 775 | 1788 |
| Example 21 | Masking particle (18%) | 468 | 788 | 1536 |
| Comparative Example 9 | Core particle | 391 | 621 | 1045 |
| Example 9 | Interlayer-coated particle | 399 | 618 | 1004 |

TABLE 8-continued (Unit: μm)

|  |  | $D_{10}$ | $D_{50}$ | $D_{90}$ |
|---|---|---|---|---|
| Example 22 | Masking particle (18%) | 410 | 624 | 981 |
| Example 23 | Masking particle (24%) | 412 | 638 | 1009 |
| Example 24 | Masking particle (30%) | 430 | 665 | 1066 |

*Value in parenthesis is mass % of masking layer relative to the mass of drug-containing particle

TABLE 9

(Unit: μm)

|  |  | $D_{10}$ | $D_{50}$ | $D_{90}$ |
|---|---|---|---|---|
| Comparative Example 10 | Core particle | 391 | 621 | 1045 |
|  | Interlayer-coated particle | 376 | 586 | 953 |
| Example 25 | Masking particle (18%) | 382 | 560 | 835 |
| Example 26 | Masking particle (24%) | 390 | 576 | 874 |
| Example 27 | Masking particle (30%) | 389 | 571 | 853 |
| Comparative Example 11 | Core particle | 361 | 543 | 835 |
|  | Interlayer-coated particle | 450 | 732 | 1251 |
| Example 28 | Masking particle (12%) | 449 | 730 | 1255 |
| Example 29 | Masking particle (18%) | 451 | 715 | 1204 |
| Example 30 | Masking particle (24%) | 457 | 701 | 1128 |
| Comparative Example 12 | Core particle | 361 | 543 | 835 |
|  | Interlayer-coated particle | 355 | 573 | 985 |
| Example 31 | Masking particle (18%) | 356 | 543 | 854 |
| Example 32 | Masking particle (24%) | 362 | 528 | 780 |
| Example 33 | Masking particle (30%) | 376 | 575 | 907 |
| Comparative Example 13 | Core particle | 361 | 577 | 1019 |
|  | Interlayer-coated particle | 417 | 664 | 1094 |
| Example 34 | Masking particle (12%) | 434 | 694 | 1192 |
| Comparative Example 14 | Core particle | 361 | 577 | 1019 |
|  | Interlayer-coated particle | 404 | 636 | 1050 |
| Example 35 | Masking particle (12%) | 413 | 641 | 1037 |
| Example 36 | Masking particle (18%) | 415 | 655 | 1087 |
| Comparative Example 15 | Core particle | 394 | 483 | 591 |
|  | Interlayer I-coated particle | 317 | 464 | 679 |
|  | Interlayer II-coated particle | 406 | 537 | 725 |
| Example 37 | Masking particle (30%) | 457 | 573 | 729 |
| Example 38 | Masking particle (36%) | 472 | 593 | 744 |
| Example 39 | Masking particle (42%) | 460 | 588 | 757 |
| Comparative Example 16 | Core particle | 58 | 101 | 147 |
|  | Drug layer-coated particle | 81 | 109 | 145 |
|  | Interlayer I-coated particle | 88 | 118 | 157 |
|  | Interlayer II-coated particle | 101 | 131 | 170 |
|  | Interlayer III-coated particle | 134 | 160 | 191 |
| Example 40 | Masking particle (54%) | 163 | 187 | 217 |
| Example 41 | Masking particle (66%) | 165 | 190 | 220 |
| Example 42 | Masking particle (78%) | 169 | 198 | 231 |

*Value in parenthesis is mass % of masking layer relative to the mass of drug-containing particle

TABLE 10

(Unit: μm)

|  |  | $D_{10}$ | $D_{50}$ | $D_{90}$ |
|---|---|---|---|---|
| Comparative Example 17 | Core particle | 58 | 101 | 147 |
|  | Drug layer-coated particle | 81 | 109 | 145 |
|  | Interlayer I-coated particle | 78 | 112 | 160 |
|  | Interlayer II-coated particle | 81 | 121 | 174 |
|  | Interlayer III-coated particle | 115 | 150 | 192 |
| Example 44 | Masking particle(54%) | 135 | 176 | 226 |
| Comparative Example 18 | Core particle | 58 | 101 | 147 |
|  | Drug layer-coated particle | 99 | 128 | 164 |
|  | Interlayer I-coated particle | 107 | 143 | 191 |
|  | Interlayer II-coated particle | 126 | 154 | 190 |
|  | Interlayer III-coated particle | 129 | 158 | 197 |
| Example 45 | Masking particle(90%) | 147 | 202 | 278 |

*Value in parenthesis is mass % of masking layer relative to the mass of drug-containing particle

INDUSTRIAL APPLICABILITY

The masking particles of the present invention do not release a drug in the mouth after taking, are unlikely to give the taste of a contained drug even having an unpleasant taste, and suppress drug absorption from the oral cavity or pharynx. After swallowing, the masking particles rapidly release a drug, and thus the drug is sufficiently absorbed from the digestive tract. The drug release suppression time can be accurately controlled to an intended time, and thus an appropriate preparation can be produced depending on the type of drug or the dosage form.

The invention claimed is:

1. Masking particles each comprising a drug-containing particle and a coating layer containing a water-insoluble polymer,
    wherein the drug-containing particle contains (i) a drug, (ii) at least one acid ingredient selected from the group consisting of an organic acid, an organic acid salt, a hydrate of the organic acid or a hydrate of the organic acid salt, and (iii) a carbonate,
    wherein the drug-containing particle is coated with the coating layer,
    wherein the content of the coating layer is 0.01-1 part by weight relative to 1 part by weight of the drug-containing particle,
    wherein a tablet is excluded from the drug-containing particle, and
    wherein $D_{50}$ of the masking particles is 1,000 μm or less.

2. The masking particles according to claim 1, wherein the carbonate is at least one water-soluble carbonate.

3. The masking particles according to claim 1, wherein the acid ingredient is contained in an amount of 0.5 to 30% by weight relative to a total amount of the drug-containing particles.

4. The masking particles according to claim 1, wherein the carbonate is contained in an amount of 0.5 to 35% by weight relative to the total amount of the drug-containing particles.

5. The masking particles according to claim 1, wherein the carbonate is contained in an amount of 0.1 to 10 parts by weight relative to 1 part by weight of the acid ingredient.

6. The masking particles according to claim 1, wherein the drug-containing particle is a uniform particle containing the drug, the acid ingredient, and the carbonate.

7. The masking particles according to claim 1, wherein the drug-containing particle comprises a portion containing the drug and a separate portion containing the acid ingredient and the carbonate.

8. The masking particles according to claim 7, wherein the drug-containing particle comprises a core particle and an interlayer on the core particle, and
    the core particle contains the drug, and the interlayer contains the acid ingredient and the carbonate, or
    the core particle contains the acid ingredient and the carbonate, and the interlayer contains the drug.

9. The masking particles according to claim 8, wherein the core particle contains a disintegrant.

10. The masking particles according to claim 8, wherein the interlayer contains a binder and/or a fluidizer or lubricant.

11. The masking particles according to claim 1, wherein the drug-containing particle comprises a portion containing the acid ingredient and a separate portion containing the carbonate.

12. The masking particles according to claim 11, wherein the drug-containing particle comprises a core particle and an interlayer on the core particle, the acid ingredient and the carbonate are separately contained in any of the core particle and the interlayer, and the drug is contained in the core particle, the interlayer, or both the core particle and the interlayer.

13. The masking particles according to claim 12, wherein the core particle contains a disintegrant.

14. The masking particles according to claim 12, wherein the interlayer contains a binder and/or a fluidizer or lubricant.

15. The masking particles according to claim 11, wherein the drug-containing particle comprises a core particle, a first interlayer, and a second interlayer, and the drug, the acid ingredient, and the carbonate are separately contained in any of the core particle, the first interlayer, and the second interlayer.

16. The masking particles according to claim 15, wherein the core particle contains a disintegrant.

17. The masking particles according to claim 15, wherein one or both of the first interlayer and the second interlayer contain a binder and/or a fluidizer or lubricant.

18. A tablet, granules, fine granules, or a powder comprising the masking particles according to claim 1.

19. An orally disintegrating tablet comprising the masking particles according to claim 1.

20. A method of controlling drug dissolution or drug release from drug-containing particles, the method comprising adding (i) at least one acid ingredient selected from the group consisting of an organic acid, an organic acid salt, a hydrate of the organic acid and a hydrate of the organic acid salt and (ii) a carbonate to the drug-containing particles, and coating the drug-containing particles with a coating layer containing a water-insoluble polymer to obtain masking particles, wherein the content of the coating layer is 0.01-1 part by weight relative to 1 part by weight of the drug-containing particle, wherein a tablet is excluded from the drug-containing particle, and wherein $D_{50}$ of the masking particles is 1,000 μm or less.

* * * * *